US010687982B2

(12) United States Patent
Fritsch

(10) Patent No.: US 10,687,982 B2
(45) Date of Patent: Jun. 23, 2020

(54) ONE-STEP TYMPANOSTOMY TUBE AND METHOD FOR INSERTING SAME

(71) Applicant: Michael H Fritsch, Indianapolis, IN (US)

(72) Inventor: Michael H Fritsch, Indianapolis, IN (US)

(73) Assignee: Domestic Legacy Limited Partnership, Indianapolis, IN (US)

( * ) Notice: Subject to any disclaimer, the term of this patent is extended or adjusted under 35 U.S.C. 154(b) by 172 days.

(21) Appl. No.: 15/897,998

(22) Filed: Feb. 15, 2018

(65) Prior Publication Data

US 2018/0235811 A1    Aug. 23, 2018

Related U.S. Application Data

(60) Continuation-in-part of application No. 15/161,379, filed on May 23, 2016, now Pat. No. 9,987,168, which is a division of application No. 13/764,875, filed on Feb. 12, 2013, now Pat. No. 9,907,699.

(60) Provisional application No. 61/668,407, filed on Jul. 5, 2012.

(51) Int. Cl.
  *A61F 11/00* (2006.01)
(52) U.S. Cl.
  CPC ............ *A61F 11/002* (2013.01); *A61F 11/00* (2013.01)
(58) Field of Classification Search
  CPC .............................. A61F 11/002; A61F 11/00
  See application file for complete search history.

(56) References Cited

U.S. PATENT DOCUMENTS

| 2,670,738 | A |   | 3/1954 | Gibbons |
| 3,592,197 | A | * | 7/1971 | Cohen .................. A61F 2/0004 |
|           |   |   |        |         604/106 |
| 3,636,943 | A |   | 1/1972 | Balamuth |
| 3,807,409 | A |   | 4/1974 | Paparella et al. |

(Continued)

FOREIGN PATENT DOCUMENTS

| EP | 0 445 946 B1 | 5/1994 |
| WO | WO2010045432 | 4/2010 |

OTHER PUBLICATIONS

PCT International Search Report dated Oct. 24, 2013 for Fritsch, International Application No. PCT/US13/50931.

(Continued)

*Primary Examiner* — Julian W Woo
(74) *Attorney, Agent, or Firm* — Indiano Law Group, LLC; E. Victor Indiano; John T. Woods

(57) ABSTRACT

A tympanostomy tube is provided for insertion into and residence in a tympanic membrane of a mammal. The tympanostomy tube has a body including a first end portion, a second end portion and a central portion disposed between the first and second end portions. Additionally, an axially extending passageway is provided having a first open end and a second open end. The first end portion includes a relatively enlarged diameter radially extending flange disposed adjacent a first end of the first end portion, and a relatively reduced diameter portion. The second end portion includes at least first and second moveable legs having first ends coupled to the first end portion and second ends. The second ends include sharpened surfaces that are sufficiently sharpened to incise through the tympanic membrane during insertion of the tympanostomy tube in the tympanic membrane.

21 Claims, 22 Drawing Sheets

(56) References Cited

U.S. PATENT DOCUMENTS

| | | | | |
|---|---|---|---|---|
| 3,897,786 | A | 8/1975 | Garnett et al. | |
| 4,043,346 | A * | 8/1977 | Mobley | A61M 25/04 604/107 |
| 4,692,142 | A * | 9/1987 | Dignam | A61F 9/00736 604/117 |
| 4,695,275 | A | 9/1987 | Bruce et al. | |
| 4,968,296 | A * | 11/1990 | Ritch | A61F 9/00781 604/164.06 |
| 5,053,040 | A | 10/1991 | Goldsmith, III | |
| 5,137,523 | A | 8/1992 | Peerless et al. | |
| 5,139,502 | A * | 8/1992 | Berg | A61M 27/002 604/264 |
| 5,178,623 | A | 1/1993 | Cinberg et al. | |
| 5,203,773 | A * | 4/1993 | Green | A61B 17/34 604/104 |
| 5,207,685 | A | 5/1993 | Cinberg et al. | |
| 5,254,120 | A | 10/1993 | Cinberg et al. | |
| 5,317,938 | A | 6/1994 | de Juan, Jr. | |
| 5,389,088 | A | 2/1995 | Hageman | |
| 5,443,493 | A | 8/1995 | Byers et al. | |
| 5,489,286 | A | 2/1996 | Cinberg et al. | |
| 5,643,280 | A | 7/1997 | Del Rio et al. | |
| 5,645,584 | A | 7/1997 | Suyama | |
| 5,775,336 | A | 7/1998 | Morris | |
| 5,827,295 | A | 10/1998 | Del Rio et al. | |
| 6,042,574 | A | 3/2000 | O'Halloran | |
| 6,045,528 | A | 4/2000 | Arenberg et al. | |
| 6,120,484 | A | 9/2000 | Silverstein | |
| 6,245,077 | B1 | 6/2001 | East et al. | |
| 6,306,114 | B1 * | 10/2001 | Freeman | A61F 9/00772 128/887 |
| 6,361,526 | B1 | 3/2002 | Reisdorf et al. | |
| 6,379,323 | B1 | 4/2002 | Patterson | |
| 6,406,453 | B1 | 6/2002 | Goode et al. | |
| 6,565,536 | B1 * | 5/2003 | Sohn | A61M 25/0074 604/174 |
| 6,648,873 | B2 | 11/2003 | Arenberg et al. | |
| 6,689,302 | B2 | 2/2004 | Reisdorf et al. | |
| 6,730,056 | B1 * | 5/2004 | Ghaem | A61F 9/00781 604/8 |
| 6,770,080 | B2 | 8/2004 | Kaplan et al. | |
| 6,936,023 | B2 | 8/2005 | Goode et al. | |
| 7,097,661 | B2 | 8/2006 | Perry | |
| 7,488,303 | B1 * | 2/2009 | Haffner | A61F 9/00781 604/521 |
| 7,704,259 | B2 | 4/2010 | Kaplan et al. | |
| 8,197,433 | B2 | 6/2012 | Cohen | |
| 8,480,610 | B1 | 7/2013 | Hill | |
| 8,480,611 | B1 | 7/2013 | Alshemari | |
| 8,529,495 | B1 | 9/2013 | Alshemari | |
| 8,568,308 | B2 * | 10/2013 | Reznik | A61B 17/3421 600/206 |
| 8,702,722 | B2 * | 4/2014 | Shahoian | A61F 11/002 606/109 |
| 8,715,244 | B2 * | 5/2014 | Prechtel | A61M 39/0247 604/175 |
| 10,285,856 | B2 * | 5/2019 | Tu | A61F 9/00781 |
| 2003/0033016 | A1 | 2/2003 | Dees, Jr. | |
| 2006/0004368 | A1 | 1/2006 | Zaleski et al. | |
| 2008/0058831 | A1 | 3/2008 | Fujiwara | |
| 2008/0058832 | A1 | 3/2008 | Fujiwara | |
| 2008/0188897 | A1 * | 8/2008 | Krebs | A61B 17/7266 606/300 |
| 2008/0215148 | A1 | 9/2008 | Lesinski et al. | |
| 2009/0209972 | A1 | 8/2009 | Loushin et al. | |
| 2009/0299379 | A1 | 12/2009 | Katz et al. | |
| 2010/0191331 | A1 | 7/2010 | Steinhardt et al. | |
| 2013/0060278 | A1 | 3/2013 | Bozung et al. | |

OTHER PUBLICATIONS

Examiner Martin T. Ton's Search Notes for Fritsch, Michael H. U.S. Appl. No. 13/764,875.

* cited by examiner

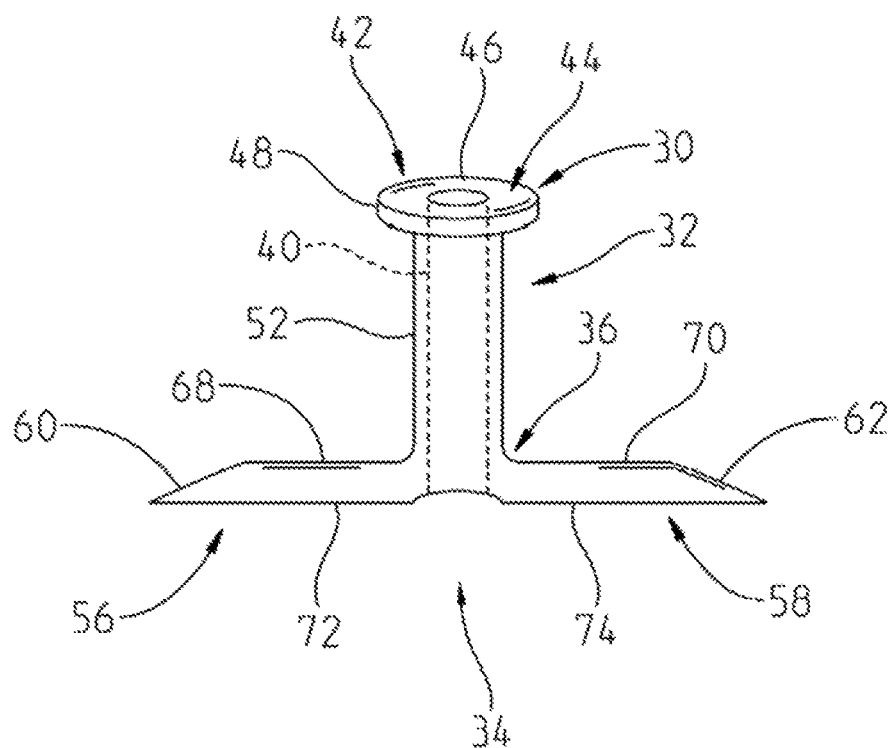
Fig. 3
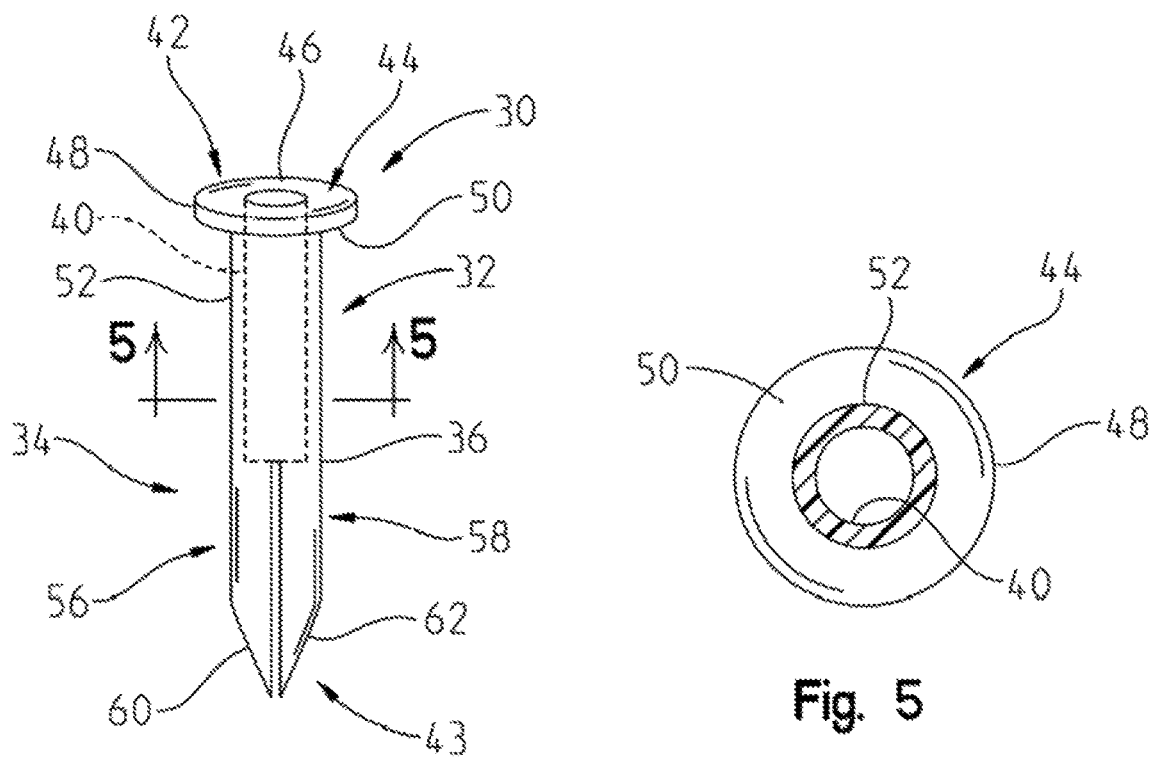
Fig. 4
Fig. 5

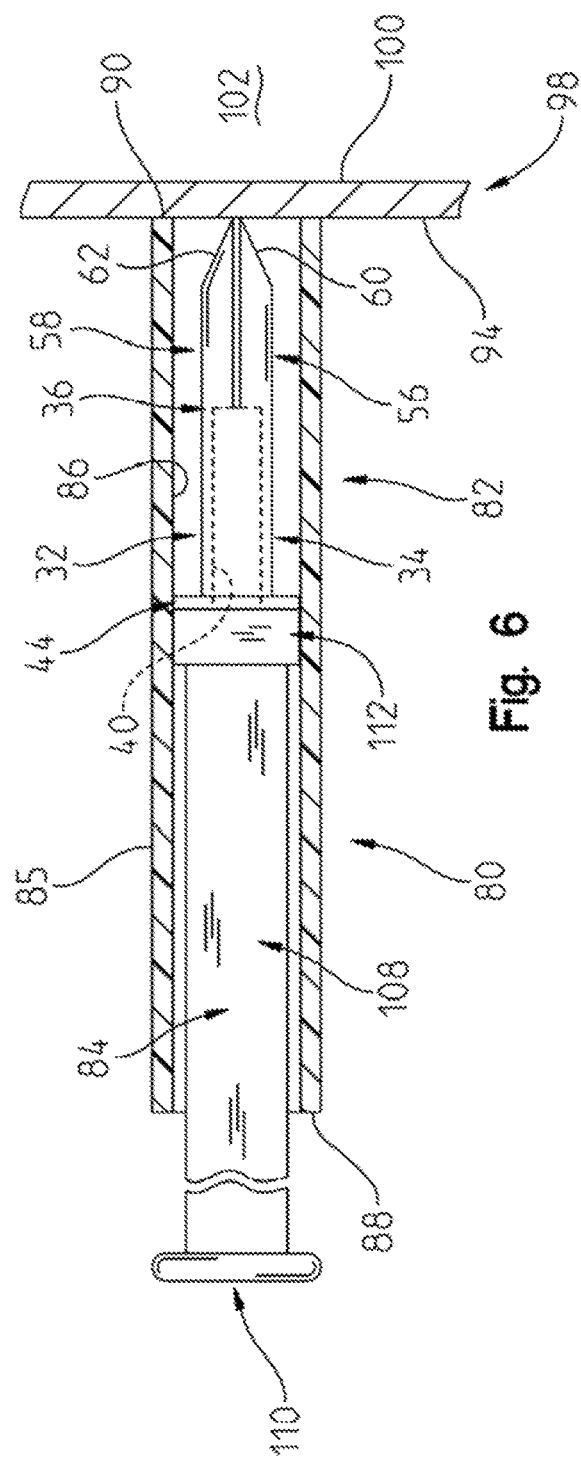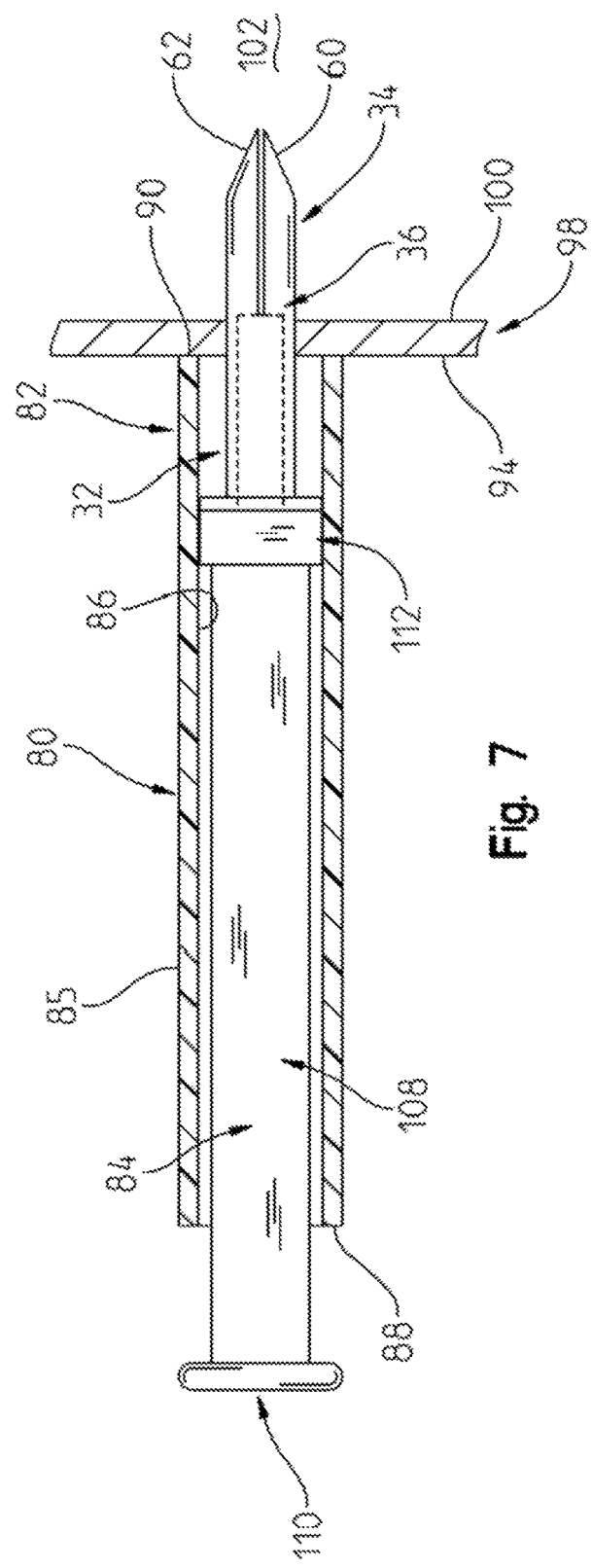

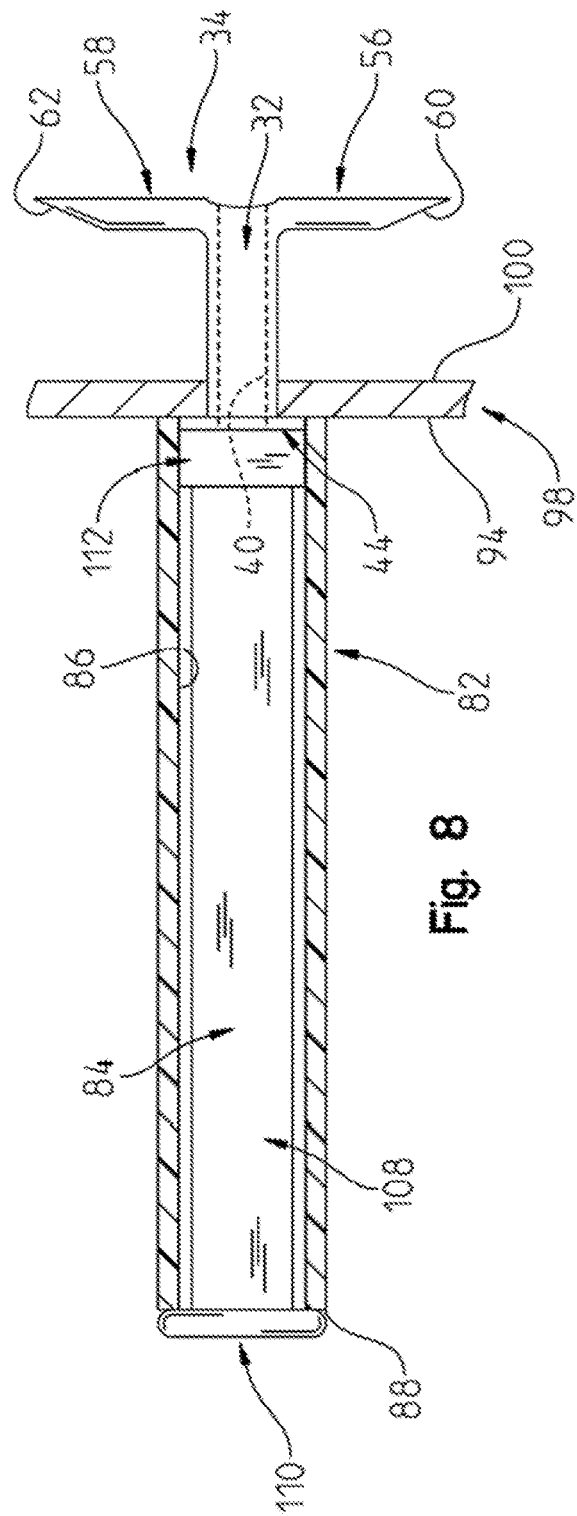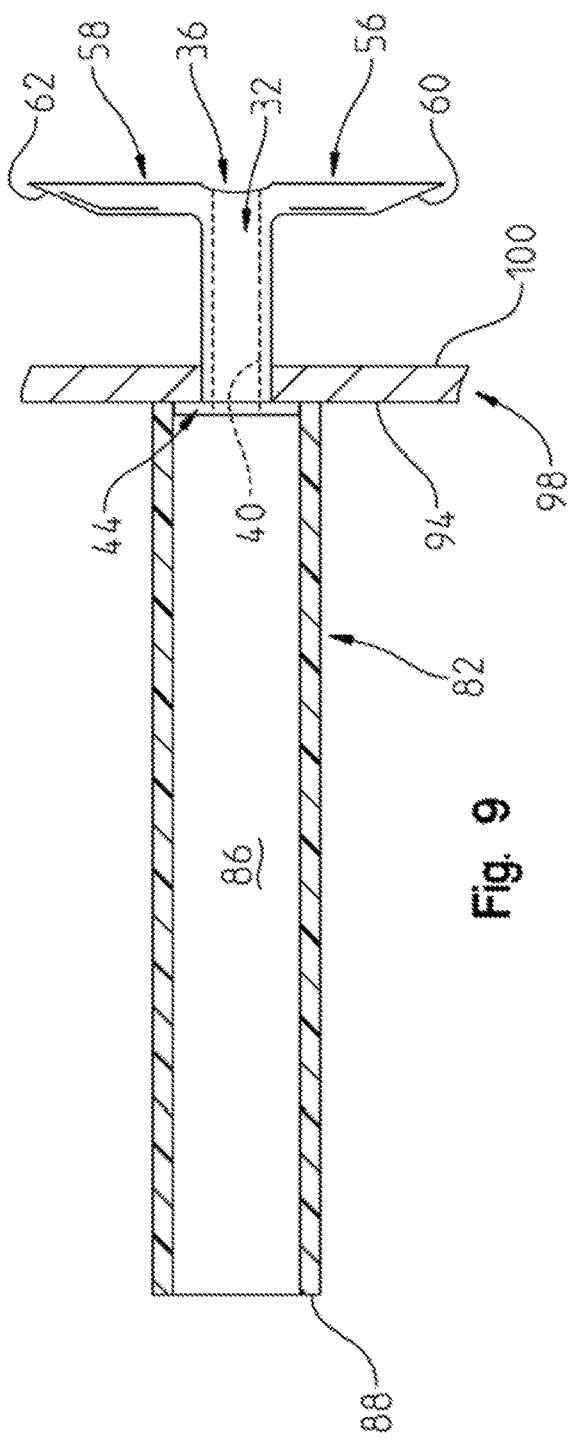

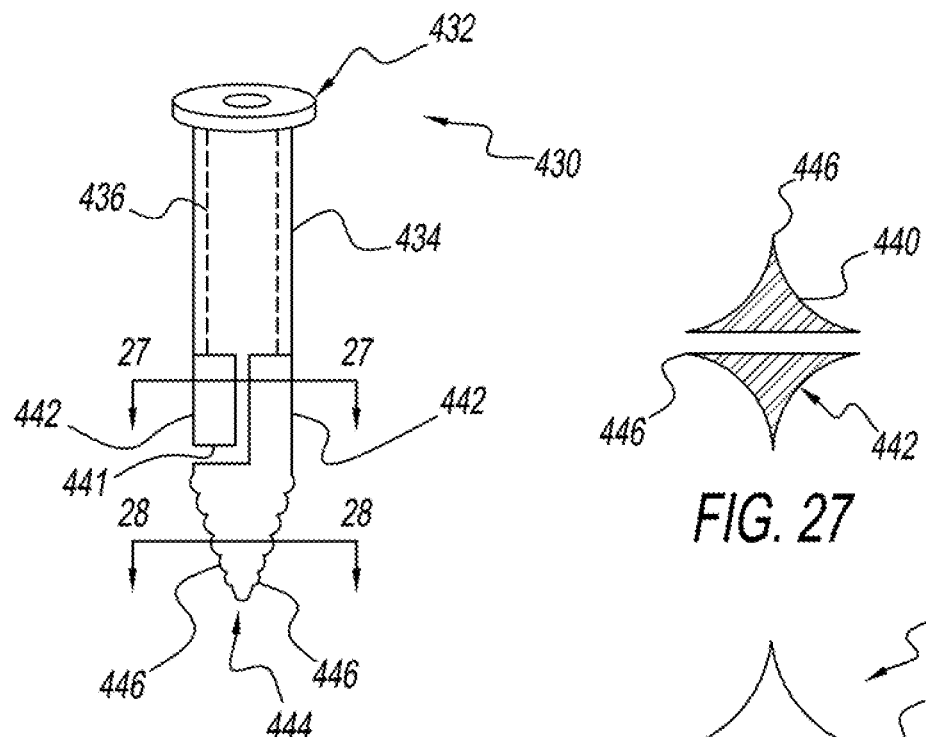
FIG. 26
FIG. 27
FIG. 28
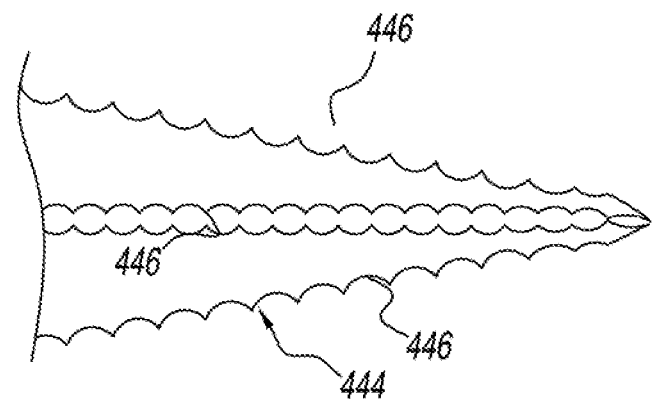
FIG. 28A

ONE-STEP TYMPANOSTOMY TUBE AND METHOD FOR INSERTING SAME

PRIORITY STATEMENT

The present application is a continuation-in-part of Michael H. Fritsch U.S. patent application Ser. No. 15/161,379, for a ONE-STEP TYMPANOSTOMY TUBE AND METHOD FOR INSERTING SAME, which was filed on 23 May 2016; which is a divisional application of Michael H. Fritsch U.S. patent application Ser. No. 13/764,875, for a ONE-STEP TYMPANOSTOMY TUBE AND METHOD FOR INSERTING SAME which was filed on 12 Feb. 2013, and which claims benefit of priority to Fritsch, U.S. provisional patent application No. 61/668,407, that was filed on 5 Jul. 2012; all of which are fully incorporated herein by reference.

I. TECHNICAL FIELD OF THE INVENTION

The present invention relates to medical devices, and more particularly, to a tympanostomy tube device used in connection with the insertion of a tympanostomy tube into a patient, and methods for inserting a tympanostomy tube in a patient.

II. BACKGROUND

From time to time, most younger children suffer from ear aches. In many cases, an earache is caused by a buildup of fluid in the middle ear that leads to an infection in the ear. Usually, the earache can be treated by giving the child an antibiotic that will help to treat this middle ear infection.

Unfortunately, antibiotics do not work well with all patients, for although the antibiotic helps to cure the infection, some patients accumulate fluid frequently enough within their middle ears so that it is necessary to Lake steps to aerate the middle ear to thereby help prevent the accumulation of fluid. This aeration helps to reduce the fluid and thereby reduce the likelihood that bacteria will cause an infection in the accumulated fluid, which thereby helps to reduce or eliminate the recurrence of earaches.

To treat such patients, a tympanostomy tube is often inserted into the eardrum to extend through the eardrum in order to keep the middle ear aerated for a prolonged period of time, and to prevent the accumulation of fluid in the inner ear. A tympanostomy tube is also known as a grommet, ear tube, pressure equalization tube, PE tube, or a myringotomy tube.

The operation to insert the tube is referred to as a myringotomy and is performed under local or general anesthesia. A myringotomy is a surgical procedure in which a tiny incision is created in the eardrum, so as to relieve pressure caused by the excessive buildup of fluid, or to drain puss, and wherein a tube is inserted in the eardrum for residence over an extended period of time.

The most commonly used type of ear tube is shaped like a grommet. If a medical practitioner decides that the ear needs to be kept open and ventilated for a long period of time, a "T" shaped tube may be used, as these "T" tubes can stay in place two to four years or so. The materials of choice for creating such tubes are plastic materials such as silicone or Teflon. Formerly, stainless steel tubes and other materials were popular, but are no longer used frequently.

The placement of ear tubes in a child's ear is a very common procedure. In the U.S., it is estimated that the most common reason for a child to undergo a general anesthetic is the insertion of such ear tubes within the child's ear. Ear tubes (tympanostomy tubes) generally remain within the eardrum for an extended period of time, usually lasting between six months and two years, although "T" tubes can last for four years or longer. Ear tubes generally spontaneously fall out of the eardrum as the skin of the eardrum slowly migrates out toward the ear canal wall over time. The ear drum usually closes without a residual hole at the tube site, but in a small number of cases, a perforation can exist.

In the conventional manner for performing tube insertion, the first step is to make a myringotomy incision by inserting a needle-like knife into the ear canal to make the incision. After the incision is made, the grommet-shaped ear tube is then grasped with forceps and half of the grommet is inserted through the incision to finally rest suspended within the eardrum, so that the passageway in the grommet creates an air passage between the auditory canal and tympanic cavity.

A typical ear tube grommet is shaped similarly to a thread spool or wire spool. The grommet generally includes a reduced diameter central portion having a cylindrical radially outwardly facing surface. A first relatively enlarged diameter flange having a cylindrical radially outwardly facing perimetral edge is placed at one end of the reduced diameter portion, and a second, similarly configured enlarged diameter portion is placed at the second end of the reduced diameter portion. An axially extending air passageway extends between a first end and a second end of the spool. The first and second end flanges also include generally planar upper and lower surfaces that have a generally round shape.

When inserted in the eardrum, the first enlarged diameter portion is disposed externally of the eardrum, with the second enlarged diameter portion disposed interiorly of the eardrum. The reduced diameter central portion extends through the eardrum. The result is that the first and second enlarged diameter portions prevent the grommet-shaped tube from becoming disconnected from the eardrum, to thus hold the grommet so that it is suspended within its position within the eardrum. When held in the proper position, the axially extending passageway of the tube can pass between the inner and outer surfaces of the eardrum, to thereby provide aeration to the middle ear, which comprises that portion of the ear that is disposed just interiorly of the eardrum.

Although such ear tubes and insertion devices serve their intended purposes well, room for improvement exists. In particular, the generally small size of an ear tube makes it very difficult and tricky to manipulate the tube properly to insert it into the eardrum. In particular, it is difficult for even skilled surgeons to line up the grommet properly to insert it into the very tiny incision that was recently made in the eardrum by the knife. In essence, the doctor must move the knife into and out of the ear to make the incision, and then follow it up with an insertion of the grommet into the ear, within the same incision that was just made by the knife.

It is therefore one object of the present invention to provide an ear tube and insertion device that provides the potential to provide a more smooth and easy ear tube insertion procedure than that known currently by the applicant.

III. SUMMARY OF THE INVENTION

In accordance with the present invention, a tympanostomy tube is provided for insertion into and residence in a tympanic membrane of a mammal. The tympanostomy tube has a body including a first end portion, a second end portion and a central portion disposed between the first and second end portions. Additionally, an axially extending passageway is provided having a first open end and a second open end. The first end portion includes a relatively enlarged diameter radially extending flange disposed adjacent to a first end of the first end portion, and a relatively reduced diameter portion. The second end portion includes at least first and second moveable legs having first ends coupled to the first end portion and second ends. The second ends include sharpened surfaces that are sufficiently sharpened to incise through the tympanic membrane during insertion of the tympanostomy tube in the tympanic membrane.

Preferably, the tympanostomy tube includes a proximal portion and a distal portion. The proximal portion is generally tubular in nature, and includes an axially-extending interior passageway. The proximal portion has an exterior diameter sized for being received within the interior axially-extending passageway of the insertion device.

The tympanostomy tube also Includes a distal portion having at least a first leg and a second leg. Each of the first and second legs include a proximal end that couples the particular leg to the distal end of the proximal portion of the tympanostomy tube, and a distal end. The distal ends of the respective at least first and second distally disposed legs are configured to saw through the tympanic membrane through the inclusion of toothed edges engageable with the tympanic membrane for sawing there through. The toothed edges of the at least first and second leg portions can comprise serrated edges surfaces capable of being moved in a back and forth direction along the surface or the eardrum to thereby permit the tympanostomy tube to be passed at least partially through the eardrum.

The toothed or serrated edges most preferably comprise rounded leading edges to increase the likelihood of the edges of the legs forming an incision in the tympanic membrane and reducing the likelihood of the serrated edge containing sawing edges tearing or rupturing the tympanic membrane.

The distill legs of the tympanostomy tube are preferably movable between an insertion position wherein the first and second legs are disposed generally coaxially with the proximal portion, and a maintenance position, wherein the first and second legs are disposed at an oblique angle to the proximal portion of the tube.

The toothed edges of the legs have the advantage of allowing the distal legs to be passed through the eardrum to a point wherein the first and second distal legs are disposed generally interiorly of the eardrum and within the tympanic cavity without requiring the making of a prior incision and the prior use of a separate knife blade. When the tympanostomy tube is inserted in the eardrum, a portion of the proximal portion of the tympanostomy tube extends through the eardrum, and the proximal end of the proximal portion is positioned generally exteriorly of the eardrum. When so positioned, the distal legs of the tympanostomy tube move from their insertion position to their maintenance position to help anchor the tube to the eardrum, to prevent the tube from becoming dislodged from the ear.

Preferably, the first and second legs are formed to be biased to normally move from their insertion position to their maintenance position. Additionally, the distal legs should be formed from a plastic having a memory so that when in the maintenance position, the distal leys extend along a line generally perpendicular to the axis of the central passageway of the proximal portion of the tympanostomy tube.

To insert the tympanostomy tube, an insertion tube is preferably placed against the exterior surface out of the eardrum. Prior to placement against the ear drum, the tympanostomy tube has been inserted into the central passageway of the insertion device, with the distal legs placed in their insertion position, such that they are disposed generally coaxially with the proximal portion. The distal edge of the legs can then be used to create an incision in the eardrum. In the toothed version, the toothed (or serrated) edge can be manipulated like a saw to move in a hack and forth direction to saw through the tympanic membrane.

The distal legs can be moved through the eardrum, to a point wherein the distal legs are disposed fully within the middle ear portion of the ear (tympanic cavity). The outward biasing of the distal legs then causes the distal legs to move from an insertion position wherein they are axially aligned with the proximal portion, to a maintenance position wherein they are preferably almost fully perpendicular to the axis of the proximal portion and forming a generally "T" shape. When the distal legs are disposed at this generally perpendicular maintenance position, the distal legs can engage the interior surface of the eardrum, to thereby make the tube resistant to removal or extrusion from the ear, or becoming dislodged from the eardrum.

In accordance with another embodiment of the present invention, a method is provided for inserting a tympanostomy tube into and for continued residence in a tympanic membrane having an interiorly facing surface in the tympanic cavity and an exteriorly facing surface in the auditory canal. The method comprises providing a tympanostomy tube comprising a body including a first end portion, a second end portion, a central portion disposed between the first and second end portions, and an axially extending passageway having a first open end disposed adjacent the first end portion, and a second open end disposed adjacent the second end portion, and an axis extending between the first open end and second open end, the first end portion including a relatively enlarged diameter, generally radially extending flange, the central portion including a reduced diameter portion, sized for extending through and residing in tissue of the tympanic membrane, and the second end portion including at least first and second movable legs having first ends coupled to the first end portion and second ends. The second ends include sharpened toothed surfaces.

Preferably, the toothed surface is placed against the exteriorly facing surface of the tympanic membrane. The tympanostomy tube is moved in hack and forth movement along the membrane to cause the toothed surface to engage the tympanic membrane and to saw through the tympanic membrane.

The tympanostomy tube is then positioned in the tympanic membrane so that the tympanostomy tube resides in the tympanic membrane with the passageway operable to conduct air between the tympanic cavity and the auditory canal.

These other features of the present invention will become apparent to those skilled in the art upon a review of the detail of the drawings appended hereto, and the detailed description of the drawings presented hereunder.

IV. BRIEF DESCRIPTION OF THE DRAWINGS

FIG. 3 is aside view of the type tympanostomy tube of the present invention, shown in its maintenance position;

FIG. 4 is a side view of the inventive tympanostomy tube of FIG. 3, shown in its insertion position;

FIG. 5 is a sectional view taken along the lines of 5-5 of FIG. 4;

FIG. 6 is a side, partly sectional view of the "T" type tympanostomy tube and insertion tools inserted in an ear canal, and just prior to the insertion of the tympanostomy tube in the tympanic membrane (eardrum);

FIG. 7 is a side, partly sectional, progressive view, showing the tympanostomy tube as it is being inserted into and extending through the tympanic membrane;

FIG. 8 is a side view of the "T" type tympanostomy tube and insertion tool of the present invention, showing the tympanostomy tube fully inserted into the tympanic membrane with the tympanostomy tube shown in its maintenance position;

FIG. 9 is a side, partly sectional view showing the tympanostomy tube fully inserted into the eardrum and in the maintenance position, with the plunger being removed from the insertion tube;

FIG. 22 is a side view of a first alternate embodiment "T" type tympanostomy tube of the present invention having a serrated cutting surface for helping to reduce tearing of the tympanic membrane when inserted there through;

FIG. 26 is a second alternate embodiment "T" type tympanostomy tube that also includes a serrated cutting surface to reduce tearing of the tympanic membrane when inserted there through;

FIG. 27 is a sectional view taken generally along lines 27-27 of FIG. 26;

FIG. 28 is a sectional view taken generally along lines 28-28 of FIG. 26;

FIG. 28A is a greatly enlarged, sectional view taken generally along lines 28A-28A of FIG. 28;

FIG. 29 is a front side view of a third alternate embodiment "T" type tympanostomy tube of the present invention having a serrated culling edge to facilitate the cutting, and reduce the tearing of the tympanic membrane as the tympanostomy tube is inserted there through;

V. DETAILED DESCRIPTION OF INVENTION

Figure 21:
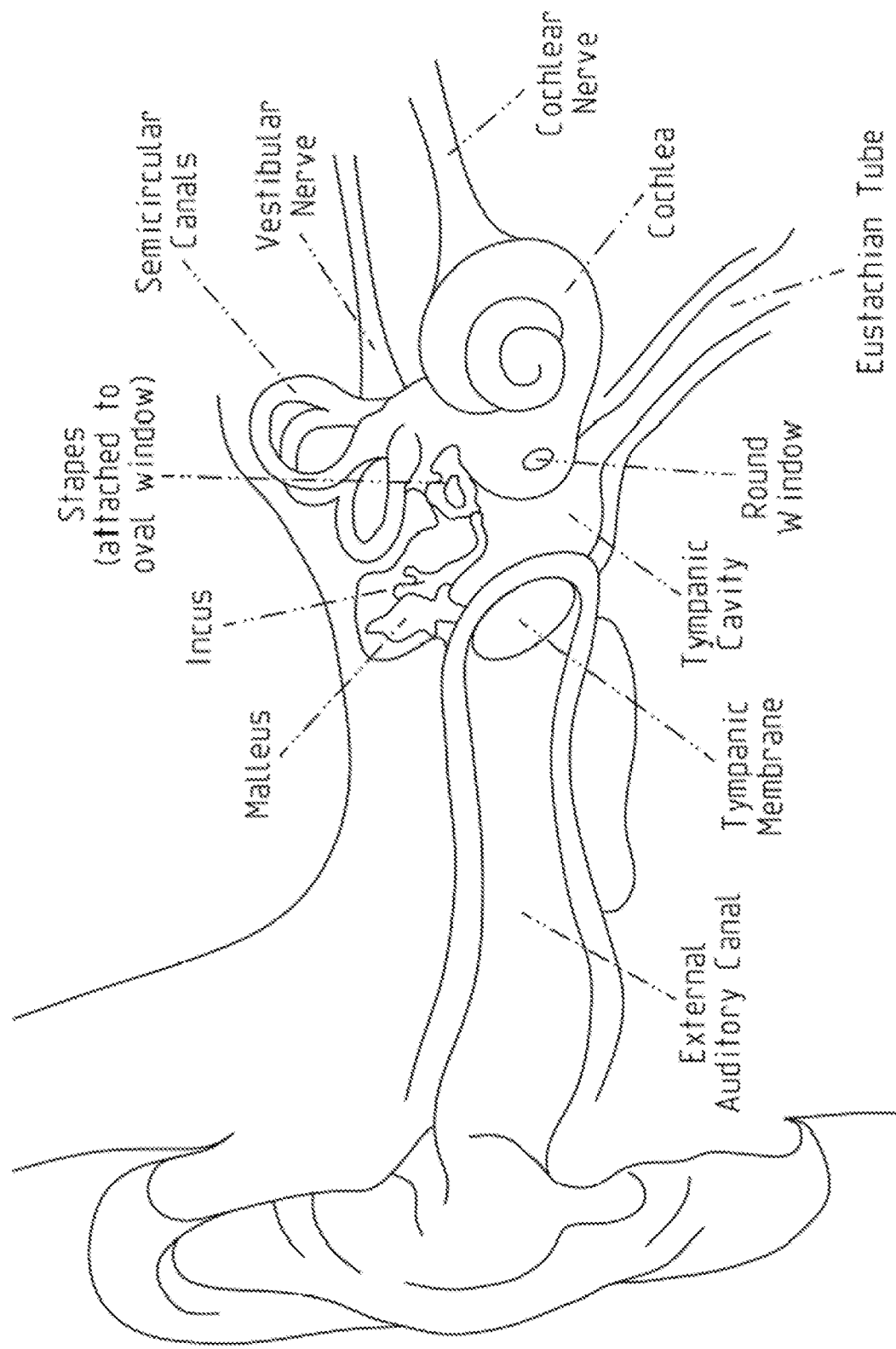
FIG. 21 is a diagrammatic view of the anatomy of the ear of a human being.
Figure 22:
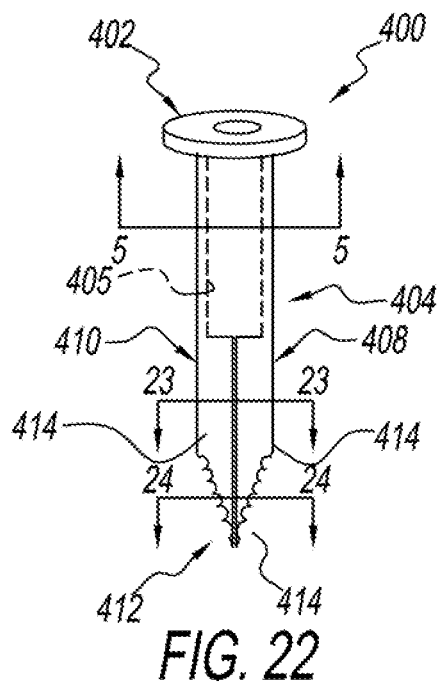

Turning first to FIG. 21, diagrammatic representation of the ear and its component parts is shown. This drawing is provided for reference to help provide context for the description of the tympanic tube of the present invention, and its placement within the ear.

The tympanic tube is inserted through the external auditory canal. The tube is positioned adjacent to the lateral (exterior) surface of the tympanic membrane, and then extended through the tympanic membrane into the tympanic cavity. The tympanic cavity is also known as the middle ear. When fully inserted and resident in the tympanic membrane, the tympanic tube will include a distal portion that is disposed adjacent to the medial (interior) surface of the tympanic membrane, and a proximal end that will be disposed adjacent to the exterior surface of the tympanic membrane, and reside in the external auditory canal.

The tympanostomy tube also includes a generally cylindrical central portion that extends through the tympanic membrane, to couple the distal and proximal ends of the tympanic ends of the tympanostomy tube. When so inserted, the tympanostomy tube of the present invention provides for aeration of the middle ear by providing a venting passageway between the external auditory canal and the tympanic cavity. This aeration helps to reduce the amount of fluid buildup in the tympanic cavity, which thereby helps to reduce the likelihood of an infection occurring in the tympanic cavity. As infections in the middle ear often result in earaches to the patient, reducing the severity and/or number of middle ear infections leads to a reduction in ear aches for the patient.

Figure 1:
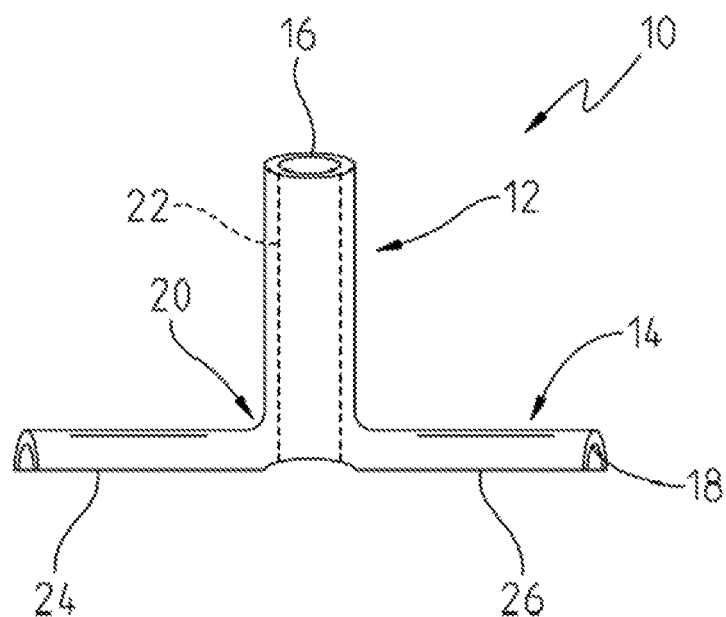
FIG. 1 is a side, partly schematic view of a prior art "T" type tympanostomy tube in its maintenance position.
Figure 2:
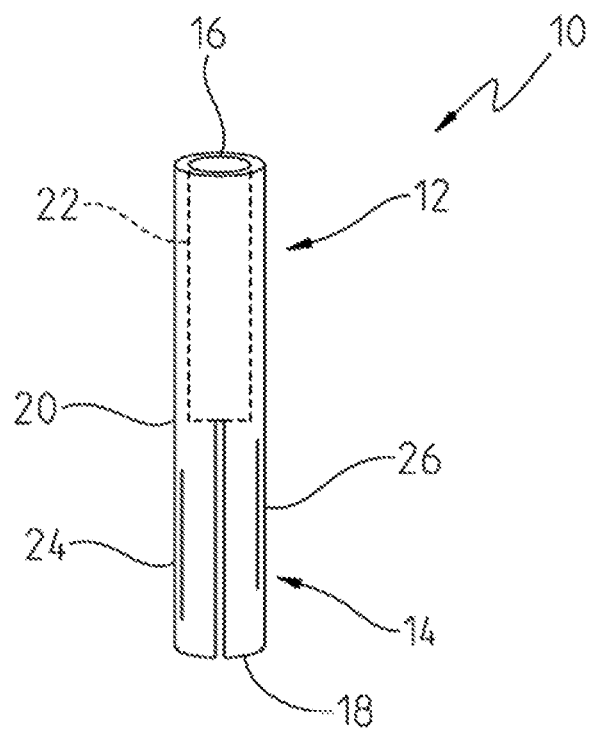
FIG. 2 is a side view of the prior an "T" type tympanostomy tube of FIG. 1 in its insertion position.

A prior known tympanostomy tube is shown in FIGS. 1 and 2. The prior tympanostomy tube 10 includes a proximal portion 12, and a distal portion 14. The tube 10 also includes a proximal end 16 that is located at the proximal end of the proximal portion 12, and a distal end 18 that is located at the distal end of the distal portion 14. A central portion 20 comprises the area of the tube 10 where the proximal portion joins the distal portion 18. An axially-extending passageway 22 extends through the proximal portion 12, and terminates at an open end in the central portion 20. When the tube 10 is in its insertion position, as shown in FIG. 2, the axially-extending passageway 22 extends all the way between the proximal end 16 and the distal end 18. The distal portion 14 includes a first axially extending distal leg member 24, and a second axially extending distal leg member 26.

When in the insertion position, as shown in FIG. 2, it will be noted that the first and second distal legs 24, 26 are disposed generally co-axially with the proximal portion 12, and that they have the same general dispositions and configurations as the proximal portion 12. However, the distal legs 24, 26 are moveable between an insertion position 14, as shown in FIG. 2, and a maintenance position as shown in FIG. 1. When in the maintenance position, the distal legs 24, 26 are disposed at generally an oblique angle, and preferably perpendicular to the axis of the axially-extending passageway 22 that extends through the proximal portion 12.

The insertion of the prior art tube 10 occurs by first employing a knife to make an incision in the tympanic membrane. The prior art tube 10 is then inserted through the freshly cut incision within the tympanic membrane to a point wherein the distal legs 24, 26 of the distal portion 14 are fully inserted into the tympanic cavity. As discussed above, this insertion procedure is a very tricky two-step procedure requiring the insertion and removal of the knife, that is followed by the insertion instrument that is used to grip and manipulate the tube, into the tympanic membrane. Once the tube 10 is successfully inserted, the instrument is removed from the ear canal.

A first embodiment "T" tympanostomy tube 30 of the present invention is shown in FIGS. 3-10. The tympanostomy tube 30 includes a proximal portion 32, a distal portion 34, and a central portion 36. The central portion 36 comprises that portion wherein the distal portion 34 joins the proximal portion 32.

An axially-extending passageway 40 extends axially through the proximal portion 32. When the tube 30 is in its insertion position, as shown in FIG. 4, the axially-extending passageway 40 also extends through the distal portion 34. The tube 30 also includes a proximal end 42 that is disposed at the proximal end of the proximal portion 32, and a distal end 43 that is disposed at the distal end of the distal portion 34.

A radially outwardly-extending flange 44 is formed at the proximal end 42 of the ear tube 30. The radially outwardly-extending flange includes a proximally-facing end surface 46, and a radially outwardly facing perimetral edge 48. An axially distally-facing surface 50 is disposed in an opposed relationship to the proximally-facing end surface 46.

The radially extending flange 44 is designed to have a diameter larger than the incision made by the tympanostomy tube 30. The purpose of this larger diameter is to ensure that the tympanostomy tube 30 remains in its appropriate place on the tympanic membrane after insertion. The relatively enlarged diameter flange 44 helps to ensure that the tympanostomy tube is not moved medially out of its engagement with the incision in the tympanic membrane, and through the tympanic membrane into the tympanic cavity.

The proximal portion 32 includes an axially-extending radially outwardly-facing generally cylindrical surface 52, which extends generally from the proximal end to the distal end of the proximal portion 32.

The distal portion 34 includes at least two distally disposed legs including a first distal leg 56 and a second distal leg 58. The first and second distal legs 56, 58 include, respectively first and second distal ends 60, 62. The first and second distal ends 60, 62 are beveled or otherwise configured to have knife like sharp edge surfaces, that comprise cutting surfaces. The first and second distal legs 60, 62 should have distal ends 60, 62 that are designed to be sharp enough to easily penetrate the tympanic membrane 98, upon the exertion of an axially and medially directed force on the tympanostomy tube 30, such as an axially-directed force that is applied to the proximally-facing surface 46 of the proximal flange 42 in a manner to move the tube 30 medially toward the tympanic cavity By employing cutting edge containing distal ends 60, 62, the need tor using a knife to make a separate incision is thereby obviated. The insertion goes from two steps (i.e. (1) an incision followed by (2) the tube insertion, to one step (i.e. incise and insert, all in one). As best shown in FIGS. 3 and 4, the distal legs 56, 58 are moveable between an insertion position (FIG. 4) and a maintenance position (FIG. 3). In the insertion position (FIG. 4), the distal legs 56, 58 assume a position wherein they are disposed generally co-axially to the long axis of the passageway 40. In the insertion position, the cutting edges 60, 62 are positioned to cut into a membrane, such as the tympanic membrane, upon an axially, medially exerted force upon the tympanostomy tube 30.

From the insertion position (FIG. 4) the distal legs 56, 58 can be moved into a maintenance position as shown in FIG. 3. In the maintenance position, the long axes of each of the first and second distal legs 56, 58 are disposed at least at an oblique angle to the long axis of the passageway 40. Preferably, as shown in FIG. 3, the first and second legs 56, 58 are disposed generally co-axially to each other, and along an axis that is generally perpendicular to the long axis of the passageway 40.

When in the maintenance position as shown in FIG. 3, the distal legs 56, 58 each include laterally (exteriorly) facing surfaces 68, 70 and medially (interiorly) facing surfaces 72, 74. The designations "medial and lateral" are used to describe these surfaces because, when in the maintenance position and inserted into an ear, the laterally-facing surfaces 68, 70 face laterally, and are disposed against the medially-facing surface of the eardrum 98. The medially-facing surfaces 56, 58 face medially inwardly in the middle ear. It will be noted that the medially/lateral designations do not necessarily apply when a device is in the insertion position (FIG. 4) as in the insertion position, the laterally-facing surfaces 68, 70 become radially outwardly-facing surfaces, and the medially-facing surfaces 56, 58 become radially inwardly-facing surfaces.

The first alternate embodiment T type tube 400 is shown in FIGS. 22-25. The first alternate embodiment T type tube 400 is constructed generally similarly to the T type tympanostomy tube 30 discussed above in connection with FIGS. 3-10, except for the fact that tube 400 has a serrated distal edge to facilitate the tube 400 incising the tympanic membrane without causing tearing of the membrane. As will be discussed in more detail below, the serrated edges facilitate the sawing through or the tympanic membrane, rather than the piercing trough of the tympanic membrane. Employing the serrated edges requires certain other modifications of the tube 400 that will be discussed in more detail below.

Figure 23:
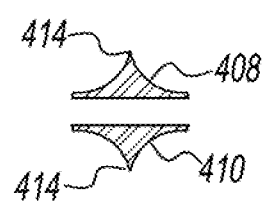
FIG. 23 is a sectional view taken along lines 23-23 of FIG. 22.
Figure 24:
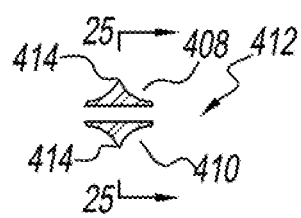
FIG. 24 is a sectional view taken along lines 24-24 of FIG. 22.
Figure 25:
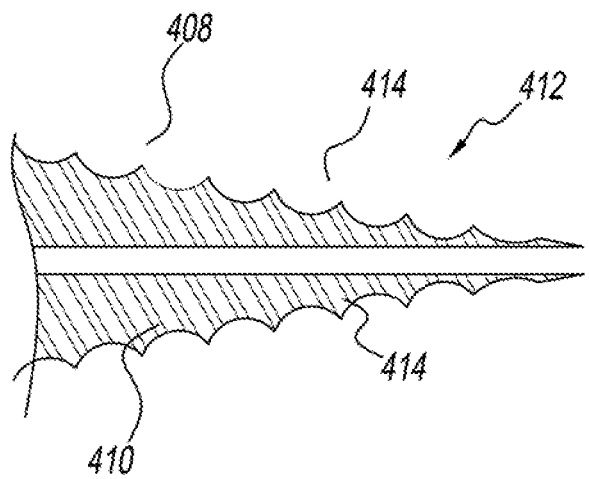
FIG. 25 is a greatly enlarged, sectional view taken generally along lines 25-25 of FIG. 24.
Figure 29:
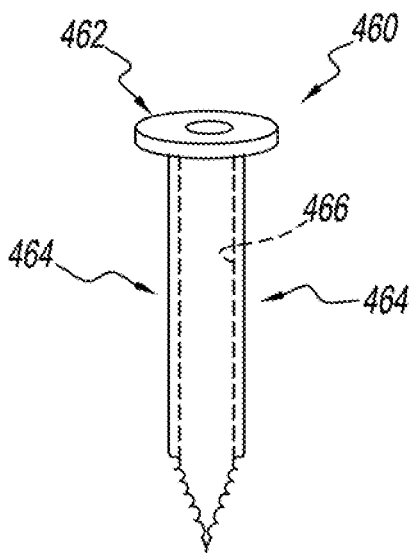
Figure 30:
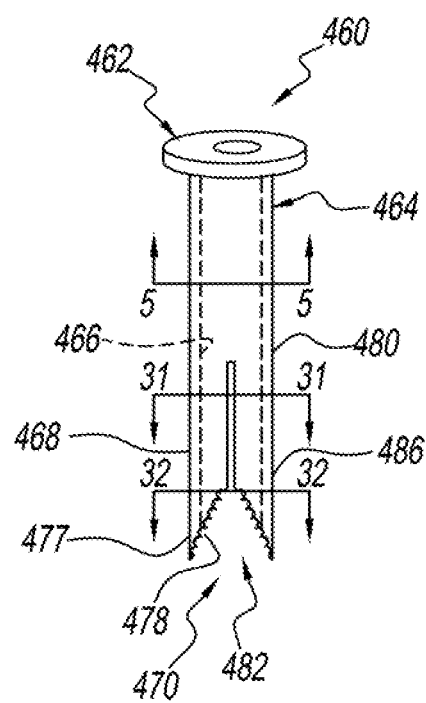
FIG. 30 is a side view of the third alternate embodiment tympanostomy tube shown in FIG. 29.
Figure 31:
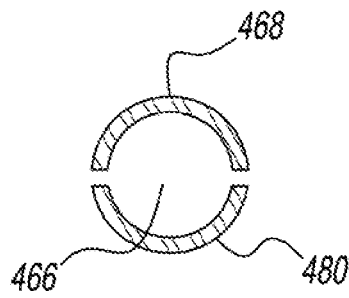
FIG. 31 is a sectional view taken generally along lines 31-31 of FIG. 36.
Figure 32:
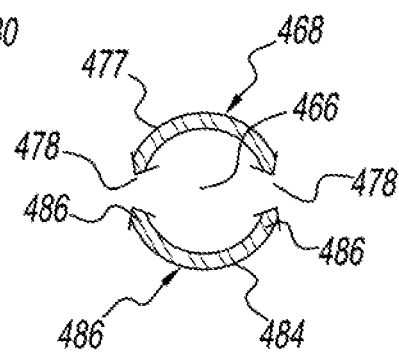
FIG. 32 is a sectional view taken generally along lines 32-32 of FIG. 30.
Figure 33:
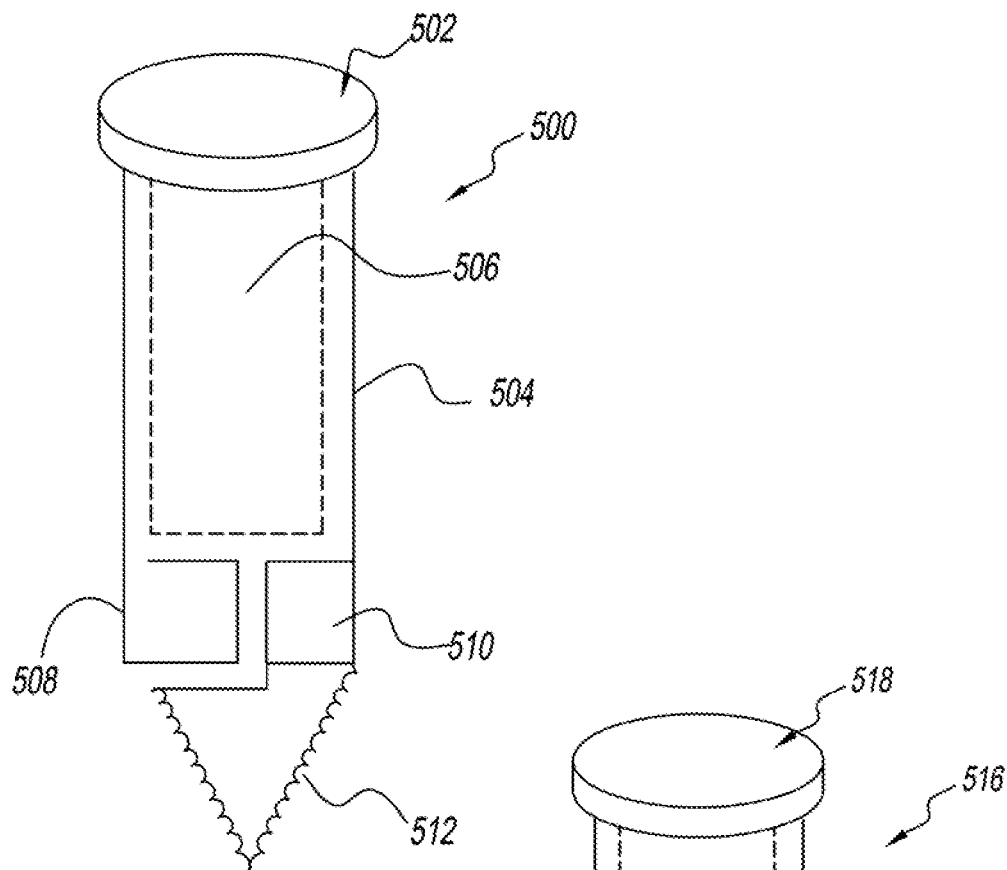
FIG. 33 is a side view of a serrated edged T-tube having solid legs shown disposed in the insertion or non-splayed position.
Figure 34:
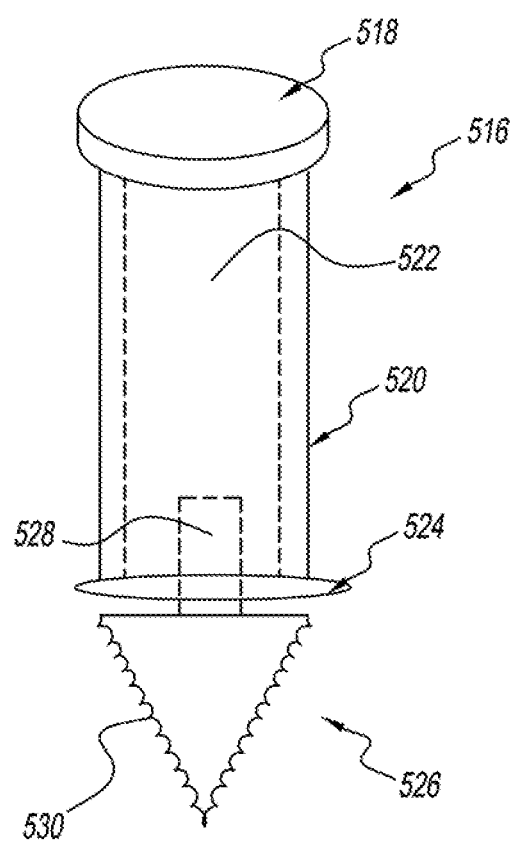
FIG. 34 is a side view of the T-tube of FIG. 33, wherein the legs are shown in their splayed, post-installation maintenance position.

The first alternate embodiment T type tube 400 includes an enlarged diameter proximal end 402, and a central portion 404. Central portion 404 includes a hollow central passageway 408 that extends generally axially through the central portion 404. The distal portion of the tube 400 includes first and second distal legs 408, 410. As illustrated in FIGS. 23-25, the first and second distal legs 408, 410 are not hollow, but rather solid to enhance their structural rigidity, to better adapt them to piercing through the tympanic membrane. The first and second distal legs 408, 410 each terminate in a pronged end 412 wherein the radius of the pronged end 412 decreases as one moves distally, so that the end has a shape reminiscent of the end of a Phillips screwdriver. The pronged end 412 includes a pair of generally axially extending serrated fins 414 having radially outwardly facing cutting surfaces.

It will be noted that the two distal legs 408, 410 are divided along a plane that extends generally from the distal end of the central portion 404, to the distal end of the pronged end 412. This planar cut results in the pronged end 412 being created from the two end portions of the respective first and second distal legs 408, 410.

A second alternate embodiment T type tympanostomy tube 430 is shown in FIGS. 26-28A as also including an enlarged diameter proximal end 432, and a central portion 434. Central portion 434 has a hollow, central passageway 436. It will be noted that a section call out is shown on FIG. 26 that suggests that the user view FIG. 5, for the section view taken along FIGS. 5-5. This use of FIG. 5 to illustrate tympanostomy tube 430 indicates that tympanostomy tube 430 is generally identical in this view with tympanostomy tube 30.

First 440 and second 442 distal legs are coupled to the distal portion of the central portion 434. The distal legs 440, 442 extend generally axially when the tympanostomy tube 430 is in its insertion portion, and are movable to extend to about a 90-degree angle when the tympanostomy tube 430 is in its inserted maintenance position.

The first distal leg 440 does not terminate at the distal end of the tympanostomy tube 430. Rather, the first distal leg 440 has a truncated, blunt cut end 441, that terminates the first distal leg 440 at a position just proximal of the four-pronged distal end 444 of the tympanostomy tube 430. This truncated blunt end 441 results in the four-pronged tapered distal end 444 being formed of a single, unitary member, as it illustrated in FIG. 28 and has a shape similar to a Phillips screwdriver with four prongs. The pronged tapered distal end 440 is formed wholly out of the second distal leg 442. The unbroken, tapered pronged distal end 444 is believed by the Applicant to enable the use of a greater number of serrated fins 446, due to the absence of a cut line.

The serrated fins 446 extend generally axially along the tapered outer surface of the tapered, four-pronged distal end 444, and have serrations that extend radially outwardly to form a radially outward extending cutting surface. As with the first alternate embodiment, the plurality of serrated fins 446 promote the cutting of the tympanic membrane by the distal conical end 444 as it incises the tympanic membrane, and reduces the likelihood of tearing of the tympanic membrane.

A third alternate embodiment T type tympanostomy tube 460 is shown in FIGS. 29-32. The embodiment shown in FIGS. 29-32 includes an enlarged diameter proximal end 462 and a central portion 464. The central portion 464 includes an axially extending, central passageway 466 that extends all the way from the opening at the proximal end 462 of the tube 460, to the distal end of the tube 460. Unlike the first and second alternate embodiments, the third alternate embodiment 460 does not include a solid distal end.

First and second distal legs 468, 480 respectively, extend distally from the generally distal end of the central portion 464. The first distal leg 468 and second distal leg 480 terminate at the distal cutting portions 470, 482 of the respective first and second distal legs 468, 480. It will be noted that the distal cutting portion 470 of the first distal leg has a generally inverted conical shape, that includes a hemi-cylindrical outer surface 477 and an angled serrated inner surface 478. Similarly, the distal end 482 also includes a generally hemi-cylindrical outer surface 484 and angled, serrated inner portion 486. As with the first and second alternate embodiments, the serrated inner surfaces 478, 486 help to better cut through the meatis of the tympanic membrane, to help reduce tearing of the tympanic membrane.

Generally, in operation and insertion, the first, second and third alternate embodiments operate generally similarly to the manner discussed above in connection with the first embodiment 30 of the T shaped tympanic tube.

Figure 35:
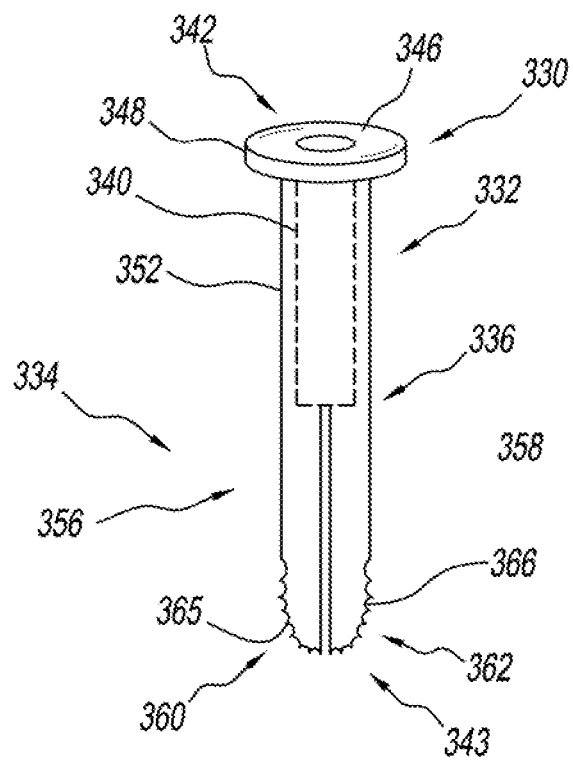
FIG. 35 is a side view of an alternate embodiment T-tube, wherein the legs are generally hollow, and the end is serrated.
Figure 36:
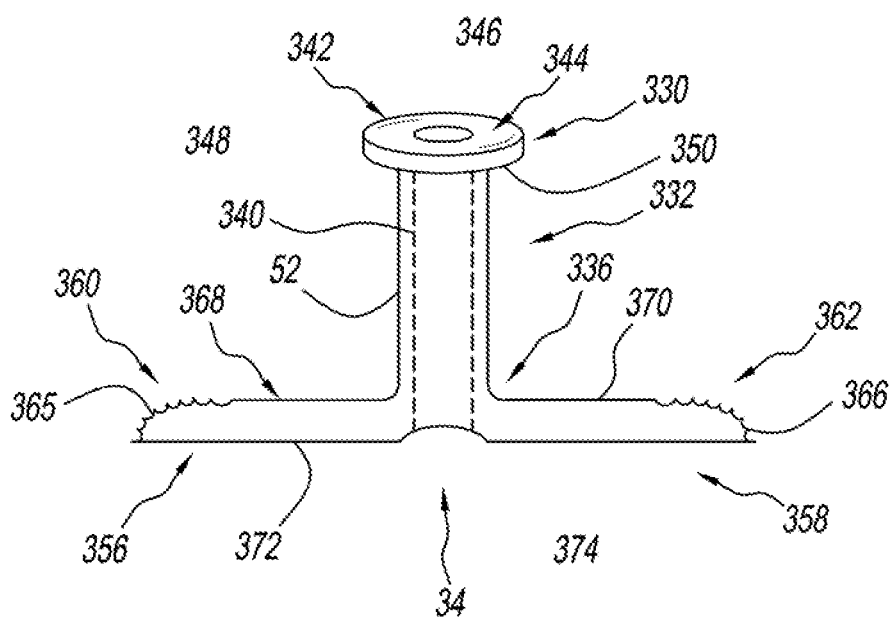
FIG. 36 is a side view of the T-tube shown in FIG. 35, wherein the legs are shown in their splayed position, as they would be when inserted into an ear of a patient through the ear drum.

A fourth embodiment "T" tympanostomy tube 330 of the present invention is shown in FIGS. 35-36. The tympanostomy tube 330 includes a proximal portion 332, a distal portion 334, and a central portion 336. The central portion 336 comprises that portion wherein the distal portion 334 joins the proximal portion 332.

An axially-extending passageway 340 extends axially through the proximal portion 332. When the tube 330 is in its insertion position, as shown in FIG. 35, the axially-extending passageway 340 also extends through the distal portion 334. The tube 330 also includes a proximal end 342 that is disposed at the proximal end of the proximal portion 332, and a distal end 343 that is disposed at the distal end of the distal portion 334.

A radially outwardly-extending flange 344 is formed at the proximal end 342 of the ear tube 330. The radially outwardly-extending flange 344 includes an axially proximally-facing end surface 346, and a radially outwardly facing perimetral edge 348. An axially distally-facing surface 350 is disposed in an opposed relationship to the proximally-facing end surface 346.

The radially extending flange 344 is designed to have a diameter larger than the incision made by the tympanostomy tube 330. The purpose of this larger diameter is to ensure that the tympanostomy tube 330 remains in its appropriate place on the exterior surface of the tympanic membrane after insertion. The relatively enlarged diameter flange 344 helps to ensure that the tympanostomy tube is not moved medially out of its engagement with the incision in the tympanic membrane, and through the tympanic membrane into the tympanic cavity.

The proximal portion 332 includes an axially-extending radially outwardly-facing generally cylindrical surface 352, which extends generally from the proximal end to the distal end of the proximal portion 332.

The distal portion 334 includes at least two distally disposed legs including a first distal leg 356 and a second distal leg 358. The first and second distal legs 356, 358 include, respectively first and second distal ends 360, 362. The first and second distal ends 360, 362 are beveled or otherwise configured to have sharpened edge surfaces, that comprise cutting surfaces. The first and second distal legs 360, 362 should have distal ends 360, 362 that are designed to be sharp enough to easily penetrate the tympanic membrane 398, upon the exertion of an axially medially directed force on the tympanostomy tube 330, such as an axially-directed force that is applied to the proximally-facing surface 346 of the proximal flange 342 in a manner to move the tube 330 medially toward the tympanic cavity.

Preferably, the distal ends 360, 362 contain toothed or serrated surfaces 365, 366. The toothed or serrated surfaces 365, 366 are provided for enabling the user to facilitate insertion of the tympanostomy tube 330 into the eardrum by moving the tympanostomy tube in a back and forth direction, to "saw" through the eardrum, rather than to pierce through the eardrum with a sharp point, as is shown by some prior art references. (See Cinberg et al., U.S. Pat. No. 5,254,120).

The Applicant, believes that the use of a serrated edge 365, 366 that is capable of sawing through the tympanic membrane, has significant advantages over the use of a sharp point that is used to pierce through the tympanic membrane. In particular, the Applicant believes that the sawing type action helps to reduce the likelihood of tearing, rupturing and damaging the tympanic membrane, when compared to a pointed device that pushes through by piercing the tympanic membrane.

To understand the advantages of this sawing motion, it is important to understand the nature of a tympanic membrane, and in particular, the mechanical aspects of the tympanic membrane. A tympanic membrane is much like a musical drum head, as it comprises tautly stretched tissue. As the name implies, an eardrum functions somewhat similarly to a drum head. In particular, vibrations caused by sounds that, occur within "hearing distance" of the eardrum, cause the eardrum to vibrate. Vibrations of the eardrum transmitted through both fluid and bone structures in the middle and inner ear.

For the tympanic membrane to function properly, it must be tautly stretched so that it is capable of vibrating in response to sound waves that strike it. If the tissue were not stretched tightly but rather was subject to movement and significant expansion and contractions, the vibrations caused by the sound wave would not be transmitted by the eardrum. Rather, the "soft, non-taut tissue" would tend to damp the vibration and not transmit the vibrations along the inner ear part.

The tautness of the eardrum carries with it the benefit of being able to transmit vibrations from the ear canal to the middle ear, and ultimately, through the bones and tissue of the middle and inner ear to the cochlea in which hair-like nerve cells pick tip vibrations and transmit the vibrations as neural output to the brain, that can then process the nerve signals into sound. However, this tautness has draw backs. In particular, because of the tautness of the eardrum, the sharp piercing of the eardrum has a propensity to result in a "stellate" fracture. This stellate fracture is a fracture that is typically characterized by a puncture point results in a plurality of radially extending tears that extend radially outwardly from the puncture point. Another example of a stellate fracture occurs when one sticks a pin in a balloon, to thereby cause the balloon to explode. A stellate fracture is also the kind of fracture that might result if one were to pierce or rupture a tightly stretched drum head.

Stellate fractures are problematic if they occur in the eardrum because stellate fractures are prone to healing with the skin cyst (cholesteatoma) from the edges of the stellate fracture. If the stellate fracture of the tympanic membrane occurs that causes a cholesteatoma, further surgeries are usually required to remove the cholesteatoma and to repair the eardrum.

By providing sawing surfaces 365, 366 that are provided on the distal end of the eardrum tube 330 of the present invention, the likelihood of such stellate fracture occurring is reduced.

The Applicant believes that the use of a back and forth movement to saw through the eardrum with a serrated surface will reduced the likelihood of stellate fractures, when compared to devices that pierce through the eardrum, such as the piercing device disclosed in Cinberg U.S. Pat. No. 5,254,120.

By employing cutting edge containing distal ends 360, 362, the need for using a knife to make a separate incision is thereby obviated. The insertion goes from two steps (i.e. (1) an incision followed by (2) the tube insertion, to one step (i.e. incise and insert, all in one). As best shown in FIGS. 35 and 36, the distal legs 356, 358 are moveable between an insertion position (FIG. 35), and a maintenance position (FIG. 36). In the insertion position (FIG. 35), the distal legs 356, 358 assume a position wherein they are disposed generally co-axially to the long axis of the passageway 340. In the insertion position, the cutting edges 360, 362 are positioned to cut into a membrane, such as the tympanic membrane, upon an axially, medially exerted sawing force upon the tympanostomy tube 330.

From the insertion position (FIG. 35) the distal legs 356, 358 can be moved into a maintenance position as shown in FIG. 36. In the maintenance position, the long axes of each of the first and second distal legs 356, 358 are disposed at least at an oblique angle to the long axis of the passageway 340. Preferably, as shown in FIG. 3, the first and second legs 356, 358 are disposed generally co-axially to each other, and along an axis that is generally perpendicular to the long axis of the passageway 340.

When in the maintenance position as shown in FIG. 36, the distal legs 356, 358 each include laterally (exteriorly) facing surfaces 368, 370 and medially (interiorly) facing surfaces 372, 374. The designations "medial and lateral" are used to describe these surfaces because, when in the maintenance position and inserted into an ear, the laterally-facing surfaces 368, 370 face laterally, and are disposed against the medially-facing surface of the eardrum 398.

The medially-facing surfaces 356, 358 face medially inwardly in the middle ear. It will be noted that the medially/ lateral designations do not necessarily apply when a device is in the insertion position (FIG. 35) as in the insertion position, the laterally-facing surfaces 368, 370 become radially outwardly-facing surfaces, and the medially-facing surfaces 356, 358 become radially inwardly-facing surfaces.

Figure 37:
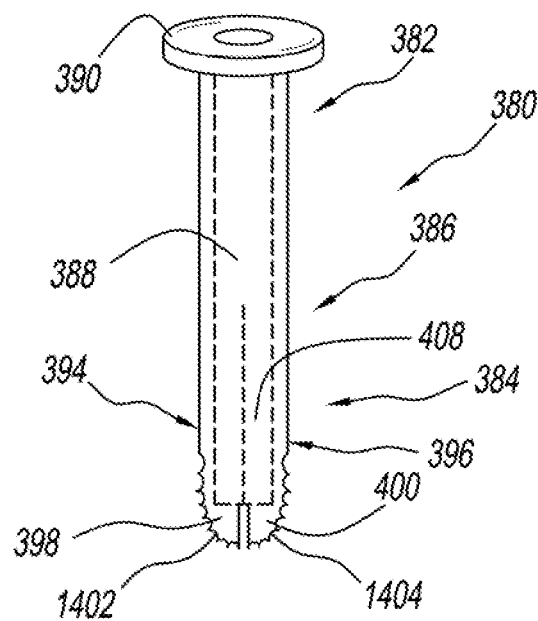
FIG. 37 is a side view of an alternate embodiment bi-pod "T-tube" of the present invention.
Figure 38:
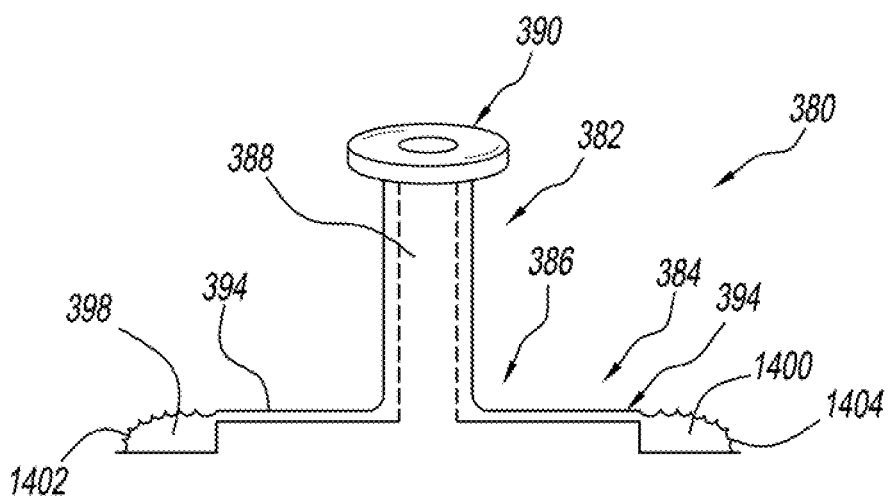
FIG. 38 is a side view of the alternate embodiment of FIG. 37, wherein the legs are shown in the maintenance position.

The third embodiment T-type tympanostomy tube 380 of the present invention is shown in FIGS. 37 and 38. Tympanostomy tube 380 includes a proximal portion 382, a distal portion 384 and a central portion 386. An axially extending passageway 388 extends between the proximal and distal ends of the tube 380, and a radially outwardly extending flange 390 is disposed at the proximal end. The distal portion 384 includes a first distal leg 394 and a second distal leg 396. The first distal leg 394 includes a first distal end 398 that includes a first toothed or serrated surface 402. Similarly, the second distal leg 398 includes a second distal end 400 that includes a second toothed or serrated surface 404.

The primary difference between tube 380 and 330 (FIGS. 35 and 36), is that the axially extending passageway 388 also includes a distal portion 408 that extends within the distal portion 384 of the tube 380.

Viewed another way, the "legs" 356, 358 of device 330 are generally solid, whereas the legs 394, 396 of tube 380 are generally hollow. However, the legs 394, 396 terminate at somewhat solid distal ends 398, 340 wherein the toothed surfaces 402, 404 reside.

A quad tube embodiment t-type tympanostomy tube 1420 of the present invention is shown in FIGS. 39-43. The quad tube tympanostomy tube 1420 includes a proximal portion 1422, a distal portion 1424 and a central portion 1426 that represents the portion wherein the proximal portion 1422 and distal portion 1424 meet. Additionally, an axially extending passageway 1428 extends through the proximal portion, and a radially outwardly extending flange 1430 is disposed at the proximal end of the proximal portion 1422. In the above respects, quad-legged tympanostomy tube 1420 is generally similar to bi-pod tympanostomy tube 380.

Figure 39:
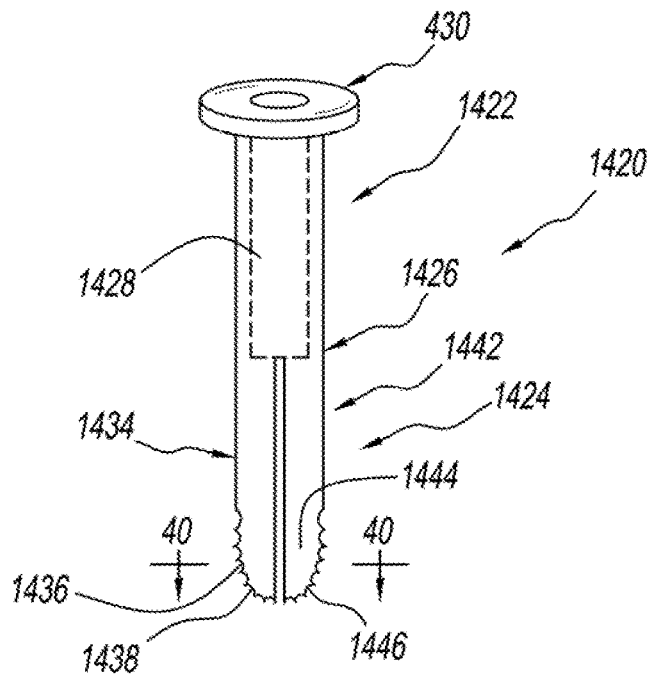
FIG. 39 is a side view of a quad leg embodiment T-tube tympanostomy tube.
Figure 40:
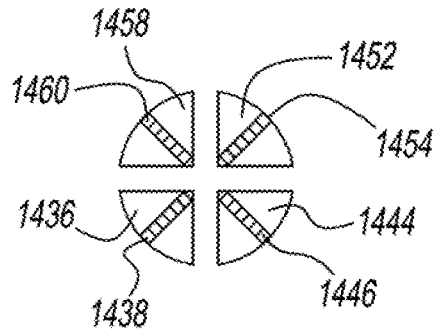
FIG. 40 is an enlarged sectional view taken along lines 40-40 of FIG. 39.

A primary difference between the quad legged tympanostomy tube 1420 and bi-pod tympanostomy tubes 380 or 330 is that the quad legged tympanostomy tube 1420 has four legs including a first distal leg 1434, a second distal leg 1442, a third distal leg 1450, and a fourth, distal leg 1456. As shown in FIG. 40, the legs 1434, 1442, 1450, 1456 are each somewhat "pie slice shaped", so that when in the insertion position 1526, as shown in FIG. 39, a generally cylindrical distal portion 1424 is formed.

The first distal leg 1434 includes a first distal end 1436 having a first toothed (serrated) surface 1438. The toothed surface 1438 extends in generally a proximal distal direction when in the insertion position, to facilitate back and forth movement of the toothed surface 1438 across the tympanic membrane, so that the first toothed surface 1438 (along with its corresponding teethed surface (1446, 1454, 1460), can form a generally linear incision in the tympanic membrane.

The second distal leg 1442 includes a second distal end 1444 and a second toothed surface 1446 that is generally similar to the first toothed surface 1438. Additionally, the third and fourth distal legs 1450, 1456 include respective third and fourth distal ends 1452, 1458, that incorporate respective third and fourth toothed (serrated) surfaces 1454, 1460 that are generally similar to the first and second distal end and first and second toothed (serrated) surfaces 1438, 1436.

Figure 41:
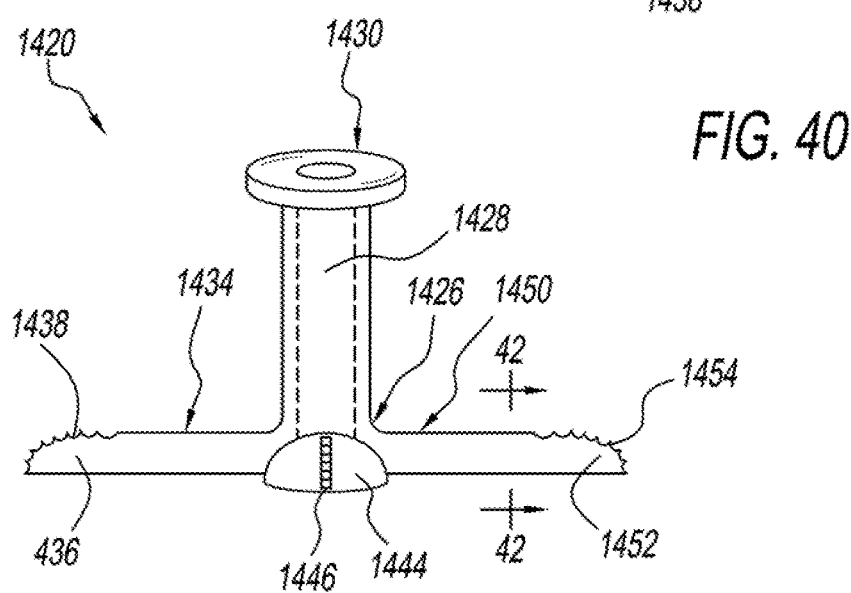
FIG. 41 is a top view of the quad legged tympanostomy tube shown with the four legs in the splayed or maintenance position.
Figure 42:
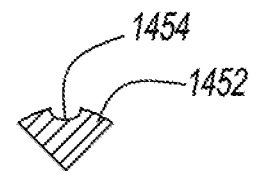
FIG. 42 is a sectional view taken generally along lines 42-42 of FIG. 41
Figure 43:
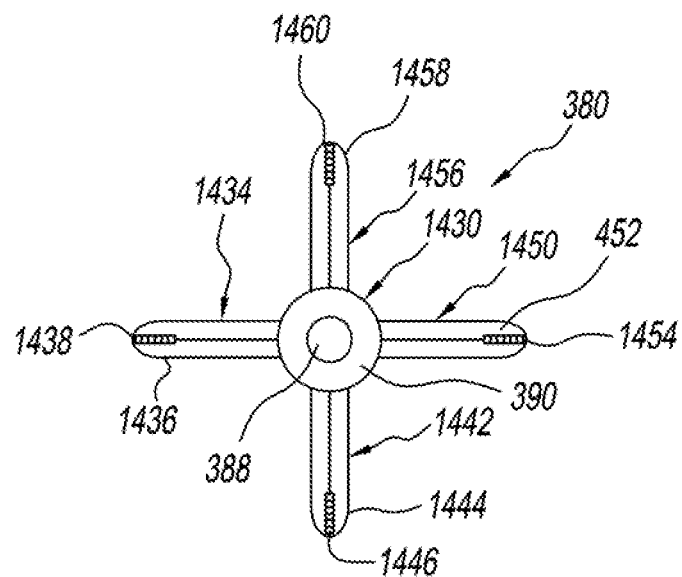
FIG. 43 is a top view of the quad tube of FIG. 40 wherein the legs are shown in their splayed or installed position.
Figure 44:
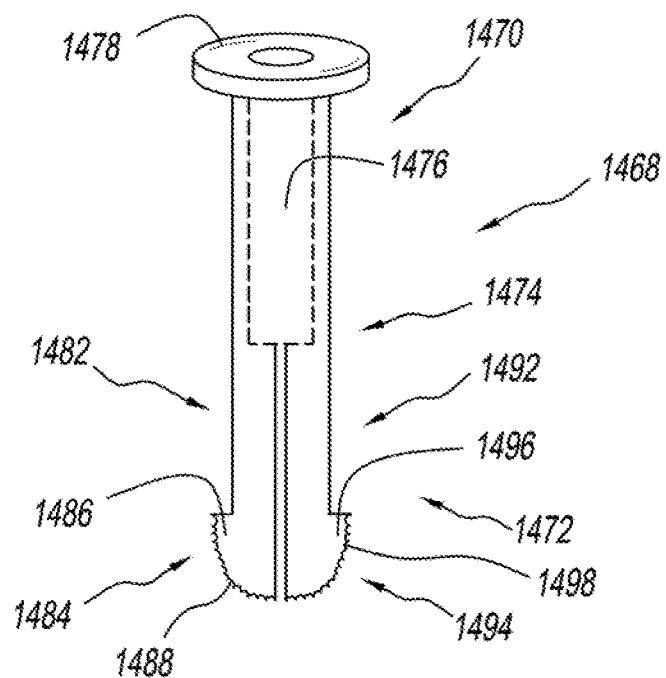
FIG. 44 is a side view of another embodiment quad-like T tube of the present invention, wherein upstanding blades having serrated or toothed surfaces are formed.
Figure 45:
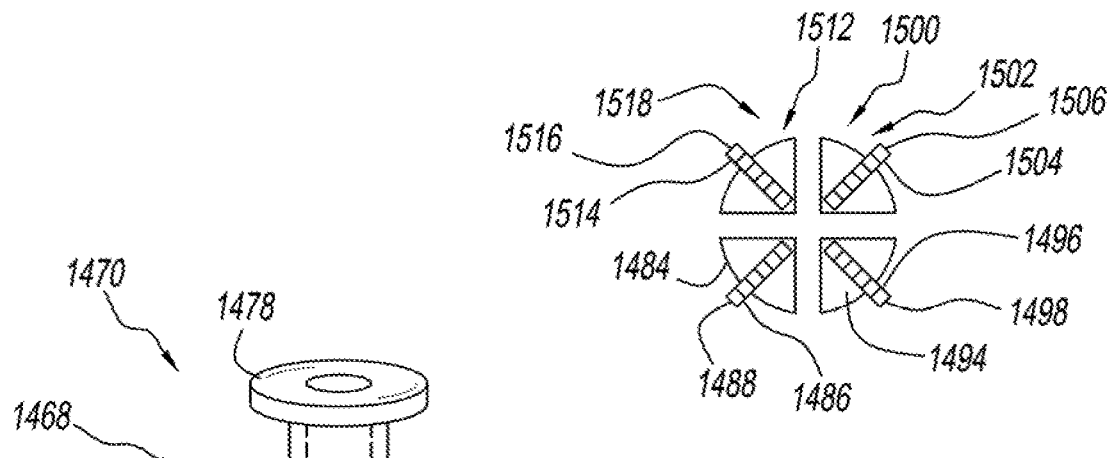
FIG. 45 is an enlarged, end view of the embodiment shown in FIG. 44.
Figure 46:
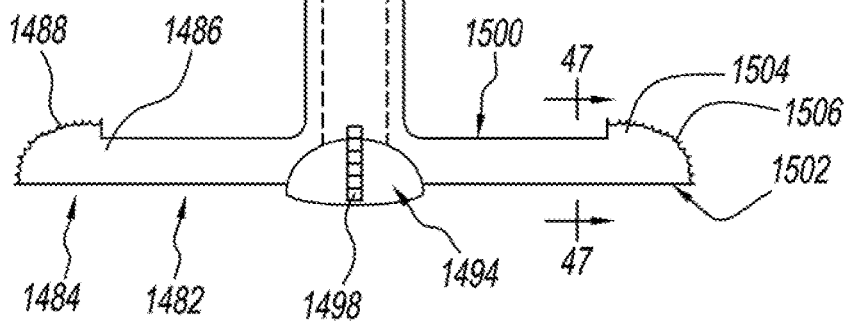
FIG. 46 is a side view of the embodiment of FIG. 42, showing the legs in the splayed, or "maintenance" position.
Figure 47:
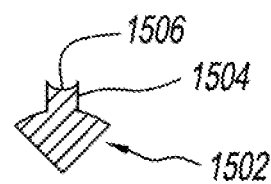
FIG. 47 is an enlarged, sectional view, taken along lines 45-45 of FIG. 44.
Figure 48:
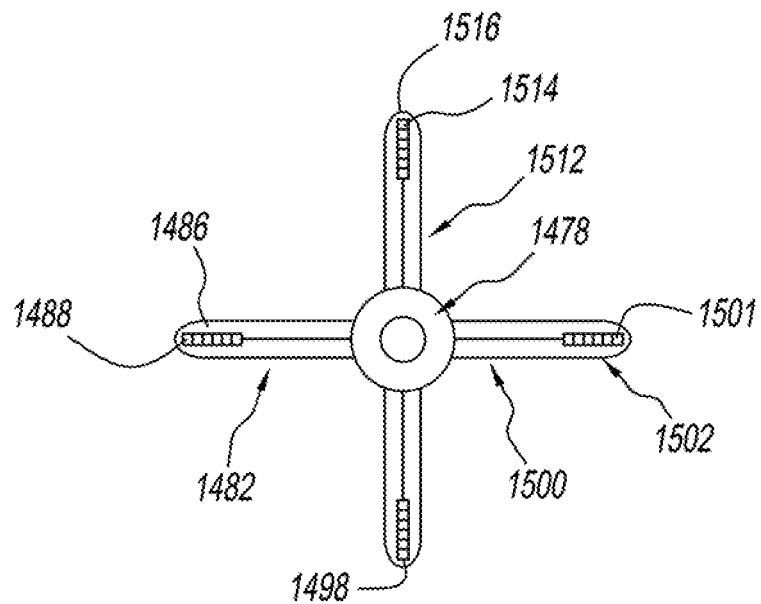
FIG. 48 is a top view of the embodiment shown in FIG. 44 wherein the legs are in their splayed position.

A benefit of the quad tube is that the use of four splayed legs when in the maintenance position, as shown in FIG. 41, is likely to provide a more stable grip on the interior surface of the tympanic membrane, to thereby be more resistant to the dislodging of the tympanostomy tube 330 from its position in the tympanic membrane when so inserted therein.

It will be noted that when in the insertion position, the toothed surfaces 1454-1438, and 1460-1466 of opposed legs are aligned so as to facilitate cutting in a back and forth direction, regardless of whether it is moving in a back and forth direction from legs one and legs three 1434, 1450 or in a back and forth direction relative to legs two and legs four 1442 and 1456.

Another quad-legged embodiment T-type tympanostomy tube 1468 is shown in FIG. 44-48. Tympanostomy tube 1468 includes a proximal portion 1470, a distal portion 1472 and a central portion 1474. An axially extending passageway 1476 extends between the proximal and distal ends of the tube 1468 and a radially outwardly extending flange 1478 is disposed at the proximal end. The distal portion 1472 includes a first distal leg 1482, a second distal leg 1492, a third distal leg 1500, and a fourth distal leg 1510.

The first distal leg 1482 includes a first distal end 1484 and a raised, blade-like portion 1486 that includes a toothed or serrated surface 1488 on the upper edge thereof. The presence of this raised blade portion 1486 is a primary distinguishing feature between the second embodiment quad legged t-tube 1468 and the first embodiment quad legged T-tube 368.

Similarly, the second distal leg 1402 includes a second distal end 1494 having a second raised blade-like portion 1496 that includes a second toothed surface 1498. Likewise, the third distal leg and fourth distal legs 1500, 1510 include respective third and fourth distal ends 1502 and 1512, that include respective third and fourth raised blade-like portions 1504, 1514 that include respective third and fourth toothed surfaces 1506, 1516.

It is believed that an advantage of the use of blade portions 1486, 1496, 1504, 1514 is that the raised blade portions 1486, 1496, 1504, 1514 are capable of better positioning the toothed surfaces 1488, 1498, 1506, 1516 on the surface of the tympanic membrane to facilitate the incising of the tympanic membrane caused by the back and sawing-like motion of the toothed surfaces 1488, 1498, 1506, 1516 of the tympanostomy tube 1468.

The method and process for inserting the tympanostomy tubes 30, 330, 380, 1470, 1420, 1468 of the present invention is best described to with respect to FIG. 6-10.

In order to insert the T-type tympanostomy tubes 30, 330, 380, 1420, 1468 into an eardrum, an insertion tool set 80 is preferably employed. The insertion tool set 80 includes a guide tube member 82, and a plunger or piston 84. The insertion tool tube member 82 is generally tube-like in configuration, and preferably has a cylindrical radially outwardly-facing exterior surface 85. A generally cylindrical radially inwardly-facing surface 86 defines an axially extending interior passageway 87 (FIG. 9) which extends between the proximal end 88 and the distal end 90 and is open at both the proximal end 88 and the distal end 90. The passageway accommodates the interiorly positioned plunger 84.

The insertion tool 80 is sized and positioned so that it can be inserted into the external auditory canal, with the proximal end 88 being disposed exteriorly outwardly of the external auditory canal by a sufficient distance so they it can be grabbed and manipulated by the surgeon. The distal end 90, when the insertion tube 80 is fully inserted, should be placeable up against, and in contact with the laterally (exteriorly) facing surface 94 of the tympanic membrane 98.

The tympanic membrane 98 generally includes a laterally (exteriorly) facing surface 94, and a medially (interiorly) facing surface 100. The laterally facing surface 94 of the tympanic membrane 98 serves as the interior terminus of the external auditory canal and the medial surface 100 serves as a wall of the tympanic cavity 102. Like a drumhead, the tympanic membrane 98 stretches across the external auditory canal.

A plunger member 84 is provided for axially moving the tympanostomy tube 30 (or 330, 380, 1420 or 1468) in an axially medially direction down the insertion tube 80. The plunger 84 may comprise something as simple as a cylindrical rod. Alternately, the rod or plunger 84 may be formed as a plunger-type mechanism that is constructed similarly to a plunger of a syringe.

One preferred feature of the plunger 84 is that it be sized appropriately. In particular, the plunger should have a flange or head member 110 that has a diameter wide than the interior diameter of the insertion tube 80. This should be done so as to enable the plunger 84 to be inserted only to a certain depth in the insertion tube 80. Preferably, the length of the plunger 84 and the length of the tympanostomy tube 80 should be complementarity sized so that at full insertion of the plunger 84, the tympanostomy tube 30 has been moved axially in a direction and to a point where the tympanostomy tube 30 is appropriately seated within the tympanic membrane 98. The plunger 84 includes a cylindrical body portion 108, a proximal end 110 that includes enlarged diameter head 110, and a distal end 112.

Turning now to FIG. 6, the tympanostomy tube 30 and plunger 84 are shown in a position wherein the insertion tube 80 is inserted into the auditory canal, to a point wherein the distal end 90 of the insertion tube 80 rests against the lateral surface 94 of the tympanic membrane 98. The tympanostomy tube 30 is shown in its insertion position wherein the distal legs 56, 58 are disposed at a generally co-axially relationship with the axis of the axially-extending passageway 40.

The plunger has its distal end 112 disposed on and engaged with the upper surface of the radially outwardly extending flange 44 of the tympanostomy tube 200, with the proximal end 110 of the plunger 84 being disposed exteriorly of the insertion tube 80. FIGS. 6 and 7 do not show the length of the plunger 84 at full scale, due to space limitations. Had these space limitations not existed, the head 110 of the plunger would be shown as extending out further from the proximal end 88 of the insertion rube 80.

FIG. 7 is a progressive view that shows that the insertion procedure has progressed to the point wherein the plunger 84 has been moved axially medially, to push the tympanostomy tube 30 axially medially. This axially medial (distal) movement of the tympanostomy tube 30 has permitted the cutting edge distal ends 60, 62 to pierce and incise the tympanic membrane 98. In the position shown in FIG. 7, the distal legs 56, 58 are in their insertion position, and the distal ends 60, 62 just barely extend through the tympanic membrane 98, so that only the cutting edges 60, 62 have emerged into the tympanic cavity 102.

In those tympanostomy tubes 330, 380, 1420, 1468 that include toothed surfaces, the distal end of the tympanostomy tubes are preferably moved in a back and forth direction along the line in which the teeth extend to incise the tympanic membrane by sawing through the tympanic membrane. As discussed above, the use of a cutting or sawing motion along the surface of the membrane incises the membrane with a lower risk of creating a stellate fracture, when compared to an incision made by a piercing movement as disclosed by the Cinberg reference cited above.

Turning now to FIG. 8, it will be noted that the plunger 84 is fully extended (to its permissible position) into the interior passageway 87 of the insertion tube 80, such that the distal end 112 of the plunger 84 is adjacent to the distal end 90 of the insertion tube 80. Note also that the distal facing surface of the plunger head 110 rests against the proximal end 88 of insertion tube 80. In this position, the radially outwardly extending flange 44 should rest against, or be close to resting against, the lateral surface 94 of the tympanic membrane 98. Additionally, the proximal portion 32 of the plunger 84 is positioned so that it is generally co-extensive with, and interiorly-disposed within the insertion tube 80.

The central portion, and the distal portion 34 of the tympanostomy tube 30 are disposed in the tympanic cavity, so that the laterally-facing surfaces 68, 70 (FIG. 3) of the distal legs 56, 58 are disposed adjacent to, and possibly resting against, the medially facing surface 100 of the tympanic membrane 98. It also should be noted that the distal legs 56, 58 have moved from their insertion position to their maintenance position. In the maintenance position, the first and second distal legs 56, 58 are disposed at an oblique angle to the axis of the central passageway 40, and preferably, are disposed generally perpendicularly to the axis of the central passageway 40.

Figure 10:
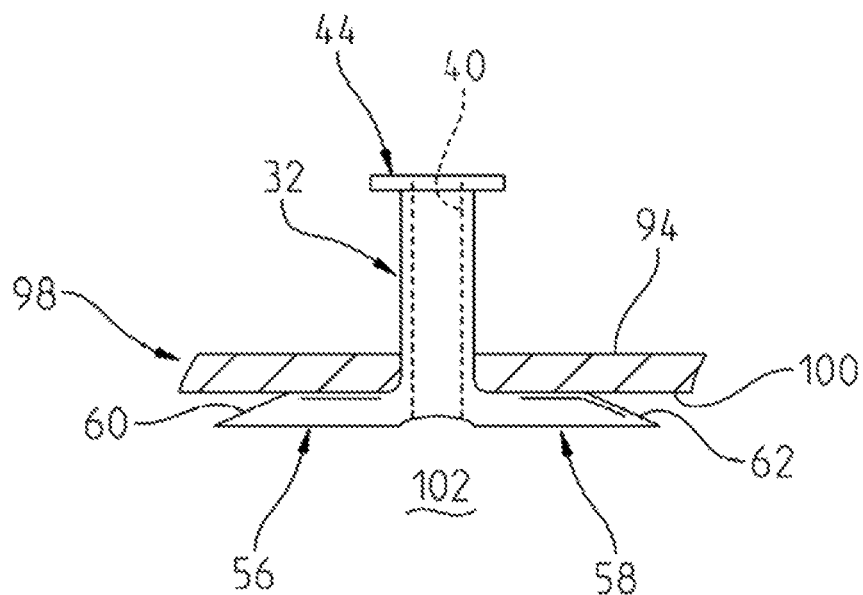
FIG. 10 is a sectional view showing the "T" type tympanostomy tube fully inserted in the tympanic membrane, with the tympanostomy tube in its maintenance position, and the insertion tube and plunger removed.

FIG. 9 is similar generally to FIG. 8. However, the plunger 84 is removed. As best shown in FIG. 10, the insertion tube 80 is also removed, and the final resting place of the tympanostomy tube 30 is shown, with the distal legs 56, 58 being moved into their maintenance position. Because of the relatively enlarged radial diameter of the proximal end flange 44, and the relatively enlarged radial diameter of the legs 56, 58, the tympanostomy tube 30 (when in the maintenance position) is prevented from moving axially within the incision in the tympanic membrane 98. The flange 44 and the legs 56, 58 thereby help to prevent the tympanostomy tube 30 from being dislodged from the tympanic membrane 98, either by sliding laterally outwardly or medially inwardly. The axially extending passageway 40 provides a vent tube between the external auditory canal and the tympanic cavity 102, to help prevent the buildup of fluid therein.

An alternate grommet embodiment tympanostomy tube 200 is shown in FIGS. 11-20. The alternate embodiment tympanostomy tube 200 includes an enlarged diameter proximal end 202, an enlarged diameter distal end 204, and a reduced diameter central portion 206.

The central portion 206 is preferably generally cylindrical in configuration and is tubular in nature. The cylindrical reduced diameter central portion 206 includes a generally cylindrical outer wall 210 and a generally cylindrical inner wall 216. Cylindrical inner wall 216 defines an axially-extending passageway 218 that has a proximal opening 220 adjacent the proximal end 202 of the tube 200, and a distal opening 222 disposed adjacent to the distal end 204.

The axially-extending passageway 218 defines a long axis of the tympanostomy tube 200. The proximal and distal openings 220, 222 and passageway 18 all open so that air can flow between the outer ear, and in particular, the external auditory canal, and the middle ear, and in particular, the tympanic cavity 102. This flow of air helps to reduce the buildup of liquid mucus and fluid in the inner ear (tympanic cavity), and thus helps to combat infections and resultant ear aches.

Figure 11:
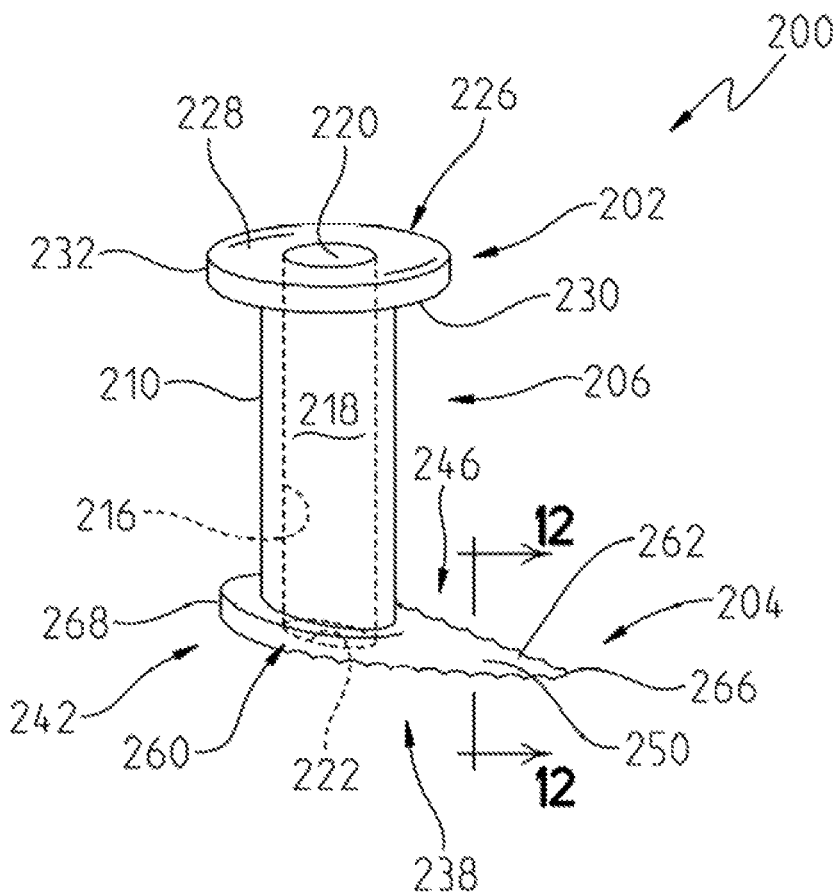
FIG. 11 is a perspective view of the first alternate embodiment "grommet" tympanostomy tube.
Figure 12:
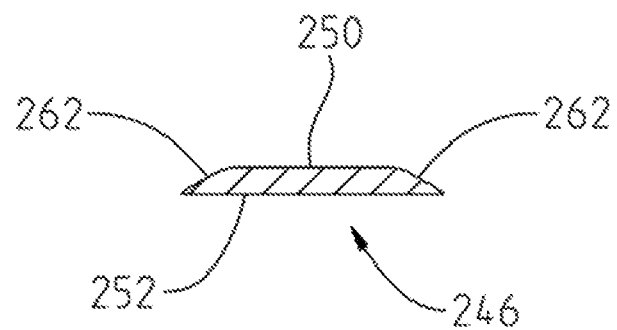
FIG. 12 is a sectional view taken along lines 12-12 of FIG. 11.
Figure 13:
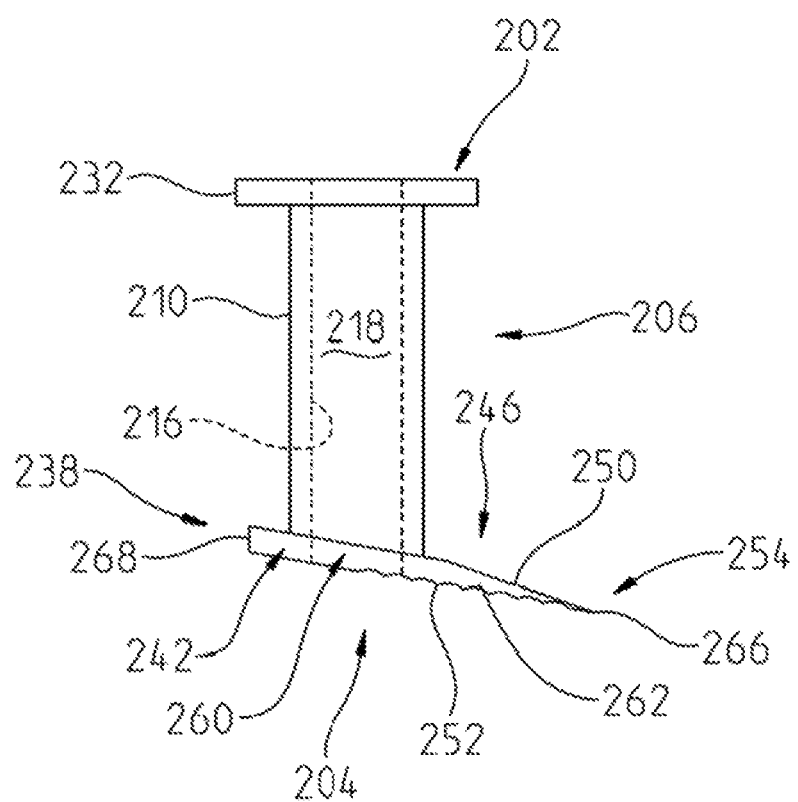
FIG. 13 is a side somewhat schematic view of the alternate embodiment tympanostomy tube shown in FIG. 11.
Figure 14:
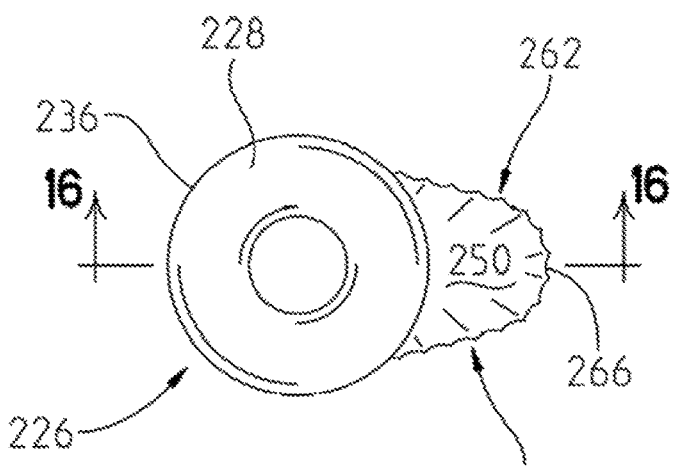
FIG. 14 is a top view of the tympanostomy tube shown in FIG. 11.

The proximal portion 202 includes a radially-extending flange 226 that includes a proximally-facing radially-extending surface 228, and an opposed, distally-facing radially-extending surface 230 (FIGS. 11, 14). The enlarged diameter radially-extending flange 226 performs a function similar to a nail head, as it helps to prevent the tympanostomy tube 200 from moving medially through the incision in which the tympanostomy tube 200 is placed. The radially-extending flange 226 also includes a radially outwardly-facing edge surface 232. Although the edge surface 232 is shown as being squared off, it can be a rounded-end surface 232 in the final device.

Figure 15:
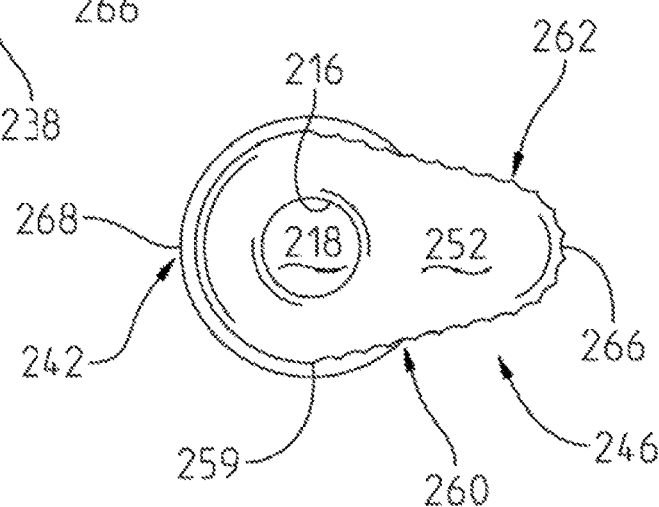
FIG. 15 is a bottom view of the tympanostomy tube grommet embodiment shown in FIG. 11.
Figure 16:
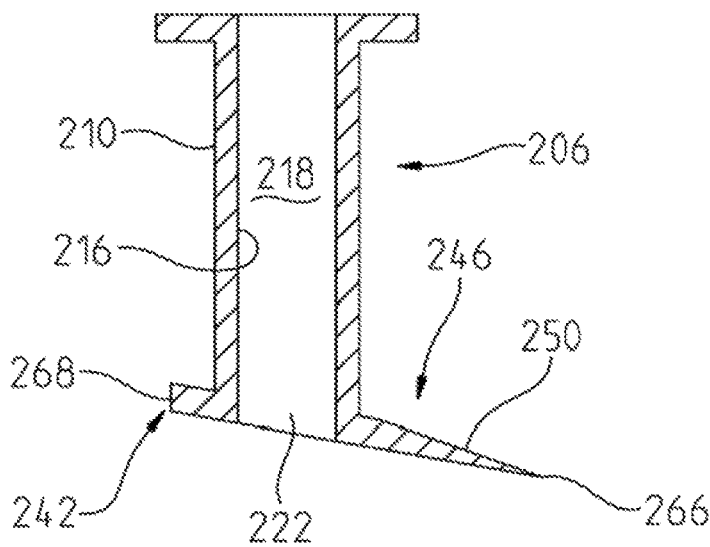
FIG. 16 is a sectional view taken along lines 16-16 of FIG. 14.

The distal portion 204 of the tympanostomy tube 202 includes an eccentric distal flange 238, that is generally ovaloid shaped in configuration. The eccentric distal flange 238 is placed in an eccentric relation relative to the axially-extending passageway 218, and central portion 206, so that the distal flange 238 includes a relatively shorter rear portion 242, and a relatively elongated forward incising portion 246 that includes an incising edge 262 of the tympanostomy tube 202 that cuts through the tympanic membrane 98, to form an incision in the tympanic membrane 98. The cutting (incising) edge 262 extends to the widest part of the ovoid distal forward incising portion 246 (FIGS. 11, 13A and 15). The tympanostomy tube 200 will simultaneously cut through and be passed through the incision to insert the tympanostomy tube 200 into the tympanic membrane 98 in one step.

It will also be noted that the tympanostomy tube's eccentric distal flange 238 is also placed at an oblique angle to the axis of the axially-extending passageway 218. Preferably, the eccentric distal flange 238 disposed at an angle up between about 110° and 150° relative to the long axis of the tympanostomy tube 200. This angled placement of the distal flange 238 helps to better position the tympanostomy tube 200 cutting edge 262 visually and economically for incising and cutting through the tympanic membrane 98.

The eccentric distal flange 238 includes an upper proximally-facing surface 250, and a lower distally-facing surface 252. The distal flange 238 includes a perimetral surface 260 that includes a forward portion 246 having a cutting edge 262, and a non-cutting edge rearward portion 268. The thickness of a distal flange 238 varies in different areas of the flange 238. Preferably, the flange 238 is designed to be generally thinner in the forward portion 246, adjacent to the knife-shaped leading edge 266, and more relatively blunted and thicker at the trailing edge 268 of the smaller rear portion 242. Most preferably, the flange 238 is knife edge like, such that the distal flange 238 is thickest at the rearward edge 268, and is beveled, such that the thickness decreases as one moves forward to the forward portion 242, with the flange 238 being at its thinnest at forward leading edge 266.

The eccentric flange 238 should be made from material than can be designed to be sufficiently rigid, and sharp at the leading edge 266, and along the entire cutting edge 262 so as to be able to cut through the tympanic membrane 98. This toughness and sharpness can be achieved with either a plastic, composite or a metal distal edge flange 238. It should be noted that the cutting edge 262 may extend along the flange 238 edge 260 from the leading edge 266 to the widest point 259 (FIG. 15) of the flange 238 to ensure better cutting characteristics. Also, the edge 262 can be formed with micro-sized teeth or serrations to improve the cutting characteristics of the device and prevent ripping or rupturing the eardrum by puncture. It should further be noted that the leading edge 266 should be rounded, rather than pointed, so that the leading edge 266 performs a controlled cut rather than a pressure puncture, rupture or shred through the tympanic membrane 98.

Figure 17:
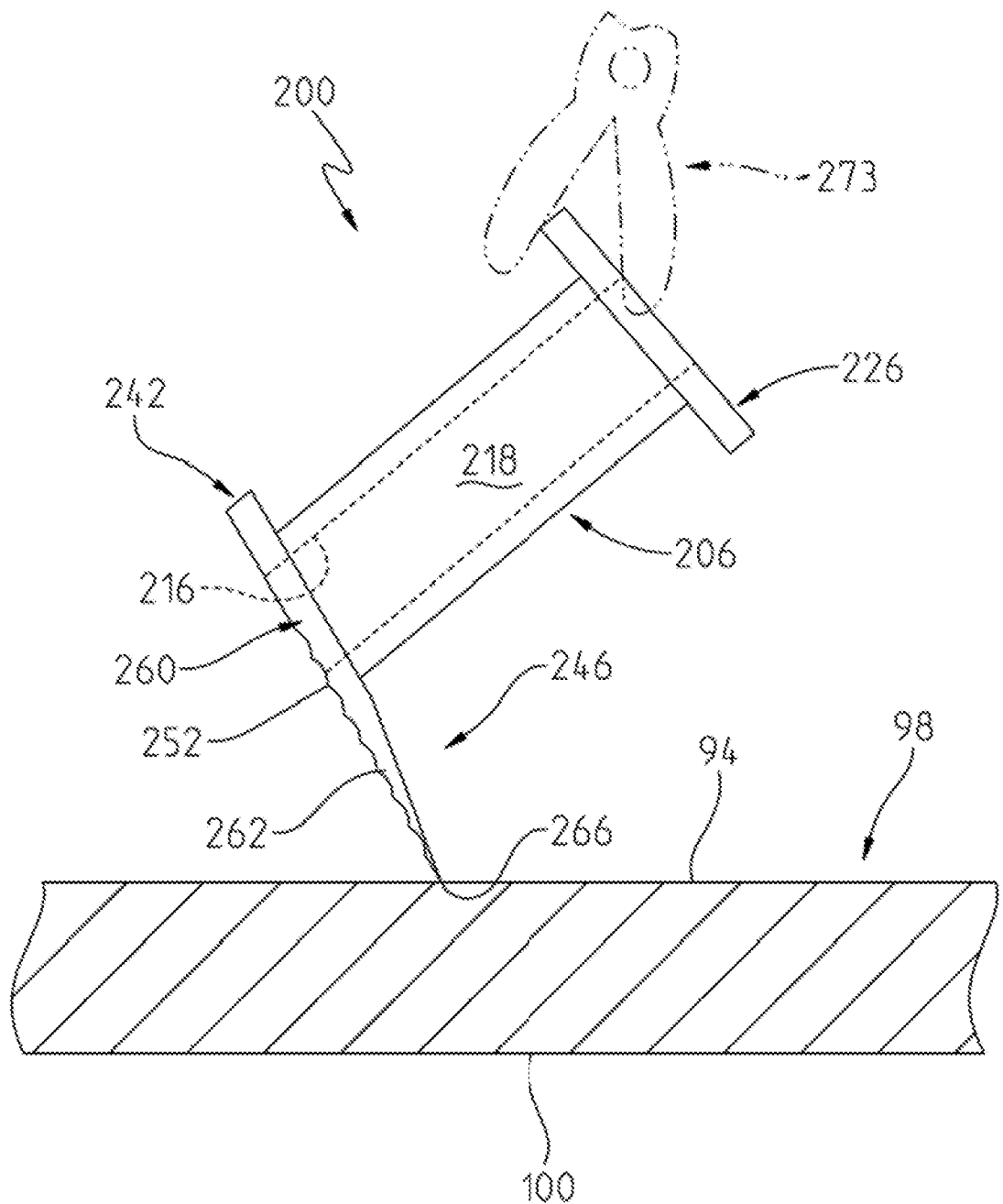
FIG. 17 is a side, partly schematic view of the grommet embodiment tympanostomy tube, showing said tube in a position where it is about to be inserted into a tympanic membrane.

The operation of the tympanostomy tube 200 will now be described with reference to FIGS. 17-20. Turning first to FIG. 17, the tube 200 is shown as being inserted in an ear canal (not shown). The proximal end 202 of the tube is gripped by forceps for so that the surgeon can manipulate the tympanostomy tube 200 into its appropriate position within the ear canal so that the distal flange 238 is placed adjacent to the lateral surface of the tympanic membrane 98. Preferably a thin forceps, such as an alligator type, Miltex micro ear forceps is employed wherein the first and second blades of the forceps are thin enough to enable the first blade to be inserted into passageway 218 to grip inner cylindrical surface 216, while the second blade is disposed exteriorly of the central portion to grip the exterior cylindrical surface 210. Through this gripping arrangement and forceps configuration, the surgeon can easily position the tube so that the long axis 218 of the tube 200 is disposed at an oblique angle, and preferably almost generally perpendicular to the plane of the laterally facing surface of the ear drum 98.

It will also be noted, that the cutting distal edge incising portion 266 is placed adjacent to the laterally-facing outer surface 94 of the tympanic membrane 98. The axis of the tube 200 (and its axially extending passageway) is held at an angle from perpendicular to the plane of the lateral surface of membrane 98, such that the axis of the axially-extending passageway 218 is disposed at an angle to the tympanic membrane 98 of approximately 45 degrees.

The forceps 273 are then manipulated by the surgeon to be moved in an axial, medial direction with micro-back-and-forth, knife-like cutting movements, toward the laterally outwardly facing surface 94 of the tympanic membrane 98, so that the leading edge 266 can cut into and cut through laterally outwardly-facing surface 94 the tympanic membrane 98. The remainder of the trailing cutting edge 262 follows and cuts its way through the incised opening of tympanic membrane 98. Preferably, the leading edge 266 of the incising edge 262 of the tube is designed to not "pierce" or "puncture" the tympanic membrane 87 since piercing or puncturing an ear drum 98 can lead to a fracture, shred or rupture of the eardrum 98. Eardrum damage that has occurred in prior art designs has caused the current preferred approach to comprise the "two-step" approach of using a knife to incise an opening into the eardrum followed by a secondary step of placing the tube in position.

Figure 18:
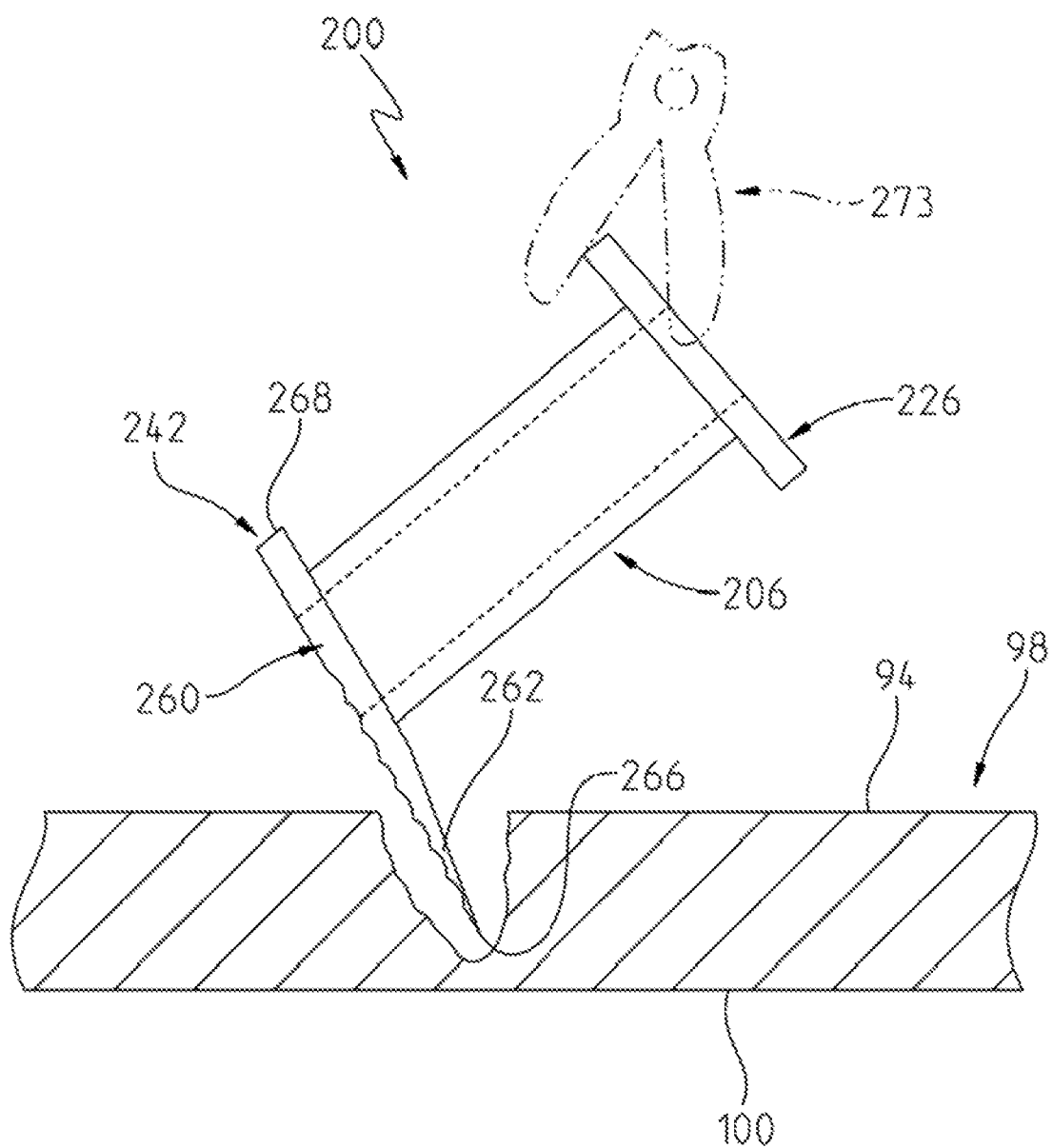
FIG. 18 is a side view, similar to FIG. 17, except that it shows the tympanostomy tube extending partially through the tympanic membrane.

The leading edge 266 generally provides the primary knife-like cutting surface, through the membrane 98. However, the entire cutting surface 262 also serves to cut the tympanic membrane in those areas of the tympanic membrane that are engaged by other areas of the cutting surface 262, as shown in FIG. 18.

Figure 19:
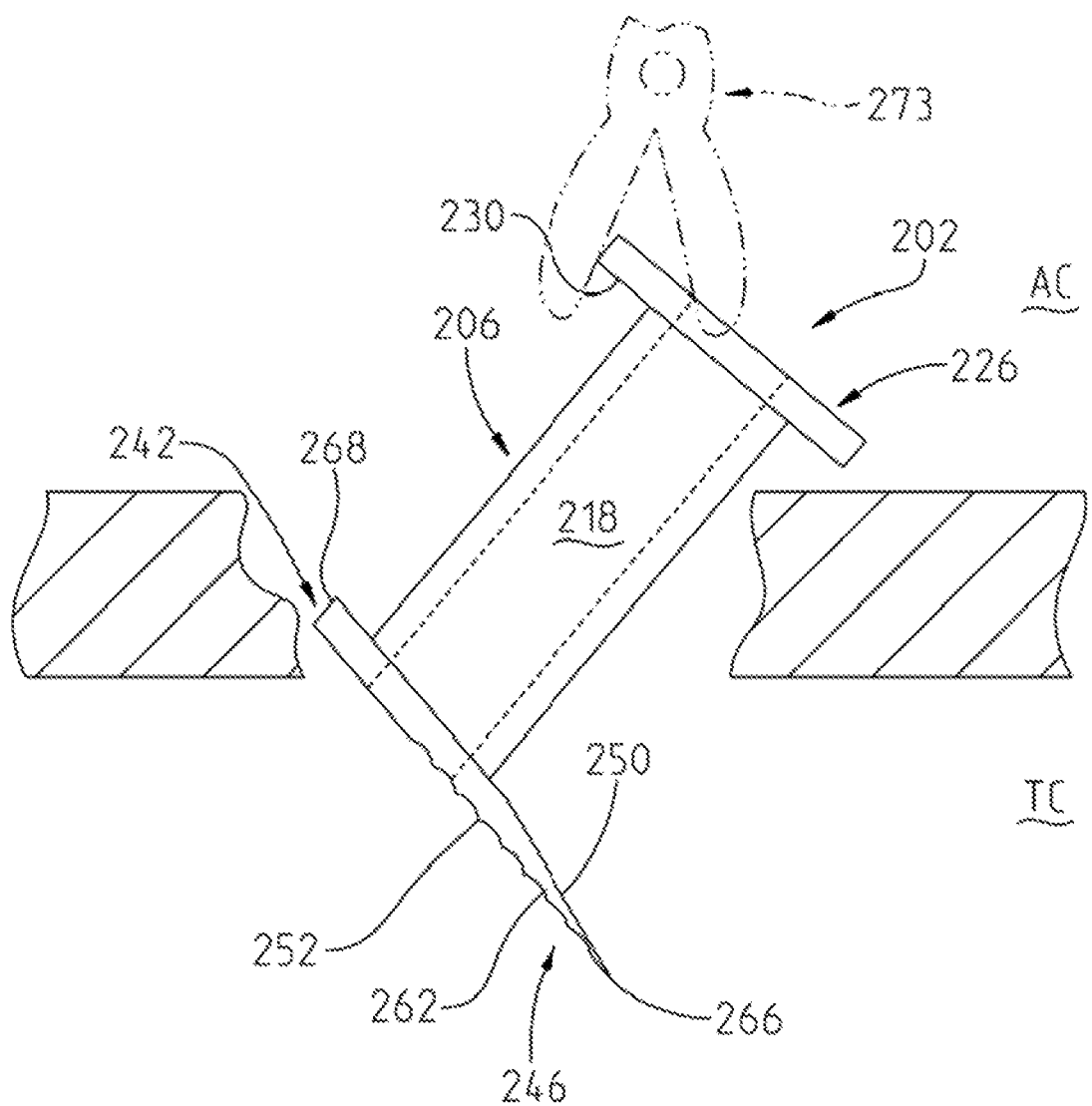
FIG. 19 is a progressive view, showing the tympanostomy tube being progressively inserted into the tympanic membrane.

Turning now to FIG. 19, the next progression shows that the forceps 273 have moved the tympanostomy tube 200 axially forwardly (and medially) to a point wherein the leading edge 266 has emerged into the tympanic cavity, TC whereas the proximal edge 202 still resides in the external auditory canal, AC. Please note that the shown width of the incision is not indicative of a high volume of tympanic material being cut away. Rather, it is envisioned that the leading edge 266 will make a slit-like incision in the tympanic membrane 98 tissue, with the tissue being cut wide enough radially outwardly to allow the flange 238 to pass through the membrane 98, and then, to permit the tissue of the tympanic membrane 98 to engage the outer cylindrical surface 210 of the central portion 206 of the tympanostomy tube 200. As the incision heals, it will snugly engage the cylindrical surface 210 to help hold the tympanostomy tube 206 in its place in the tympanic membrane 98.

Figure 20:
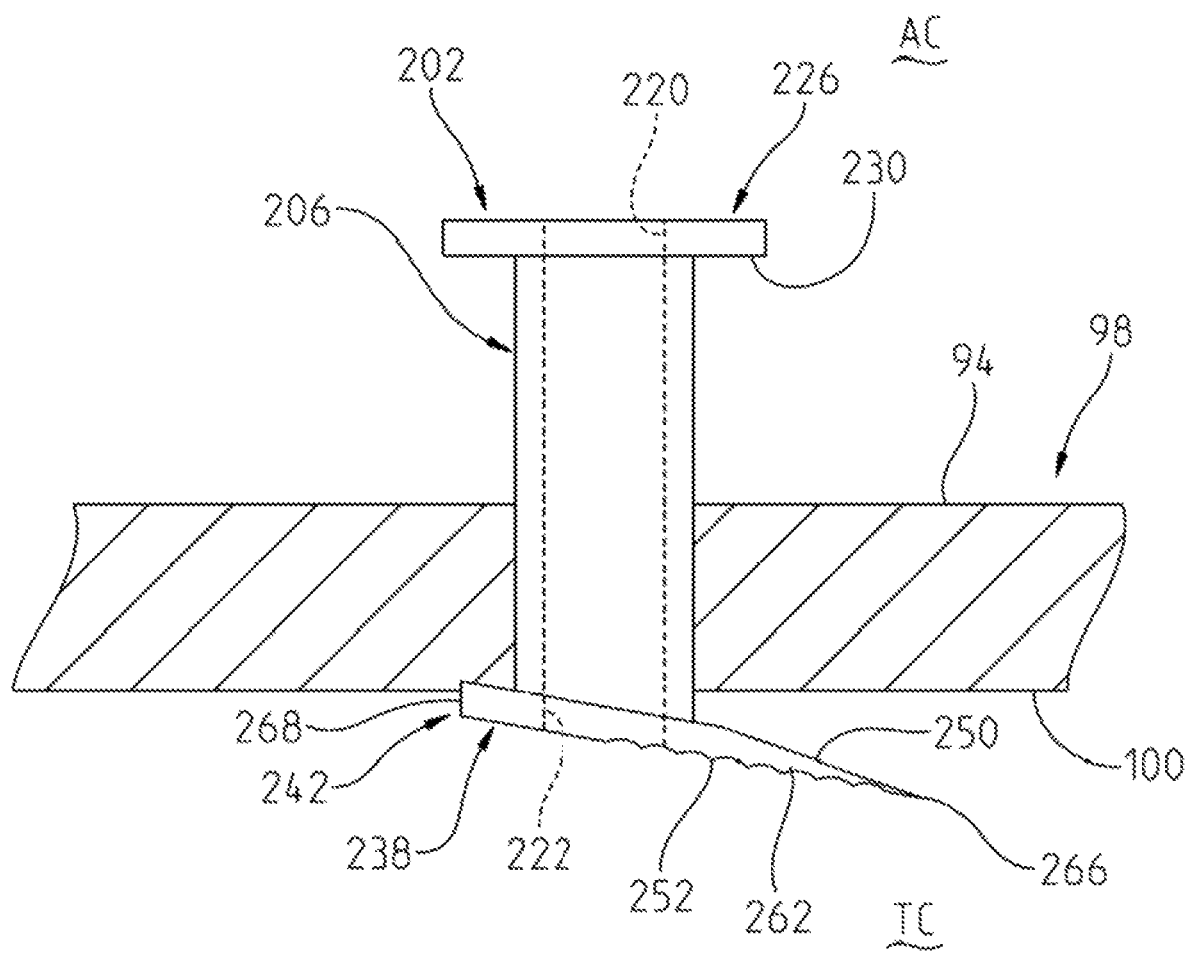
FIG. 20 is a side view, showing the grommet embodiment tympanic tube fully inserted into a tympanic membrane of the present invention.

Turning now to FIG. 20, the tympanostomy tube 200 is shown in its final position. It will be noted that the proximal portion 202 of the tympanostomy tube 200 is disposed within the external auditory canal. The proximal (first) flange 226, and in particular, the distal, medially-facing surface 230 of the proximal flange 226 rests against the lateral, outwardly-facing surface 94 of the tympanic membrane 98, As the diameter of the first flange 226 is generally greater than the diameter of the incision cut through the tympanic membrane 98, the width and diameter of the flange 226 will help to present the tympanostomy tube 200 from migrating in a medial direction into the tympanic cavity.

The distal flange 238 is inserted into the tympanic cavity 102. As the diameter of the distal second flange 238 is greater than the diameter of the incision, the distal flange 238 will help to prevent the tympanostomy tube 200 from migrating in a lateral direction out of the tympanic cavity TC, and into the external auditory canal AC. The proximal facing surface 250 engages and is placed against the medially-facing surface 100 of the tympanic membrane 98. Due to the oblique angle of the eccentric flange 238, the foreshortened rear portion 242 will more tightly and closely engage the medial surface 100 of the eardrum 98, than the more distally disposed forward leading-edge portion 246.

Having described the invention in detail with referenced certain preferred embodiments, it will be appreciated that the scope and spirit of the invention incorporates modifications, variations and equivalents of the device described herein.

The invention claimed is:

1. A medical device, comprising:
a tympanostomy tube for insertion into and residence in a tympanic membrane of a mammal, wherein the tympanostomy tube includes a body including a first end portion, a second end portion, a central portion disposed between the first and second end portions, and an axially extending passageway having a first open end and a second open end;
wherein the first end portion includes a relatively enlarged diameter radially extending flange disposed adjacent a first end of the first end portion, and a relatively reduced diameter portion; and
wherein the second end portion includes at least first and second moveable legs operably coupled to the central portion, wherein each leg includes proximal and distal portions, wherein distal portions of the first and second moveable legs include sharpened surfaces, and wherein the sharpened surfaces are configured to incise through the tympanic membrane during insertion of the tympanostomy tube in the tympanic membrane, and wherein proximal portions include non-cutting surfaces configured to contact the tympanic membrane.

2. The medical device of claim 1, wherein the axially extending passageway extends through the first end portion and central portion, and wherein the axially extending passageway includes an axis, and wherein the at least first and second moveable legs are moveable between an insertion position wherein the legs are disposed generally parallel to the axis and a maintenance position wherein the legs are disposed at one of an oblique and perpendicular angle to the axis.

3. The medical device of claim 2, further comprising a tube-like insertion tool for receiving the tympanostomy tube and for maintaining the at least first and second moveable legs in the insertion position.

4. The medical device of claim 3, wherein the insertion tool includes a tube having a passageway for receiving the tympanostomy tube, and a plunger member insertable in the tube for axially urging the tympanostomy tube into the tympanic membrane to facilitate the passage of the at least first and second legs through the tympanostomy tube and into a tympanic cavity.

5. The medical device of claim 4, wherein the plunger member is movable in a back and forth direction for permitting tympanostomy tube to incise through the tympanic membrane through a sawing action.

6. The medical device of claim 5, wherein the sharpened surfaces further comprise toothed edges configured to engage with the tympanic membrane for sawing through the membrane.

7. The medical device of claim 6, wherein the toothed edges comprise serrated edges.

8. The medical device of claim 1, wherein the at least first and second moveable legs are hingedly coupled to the central portion, and wherein the first and second moveable legs are biased to move into a maintenance position in an absence of a restraining force, and wherein in the maintenance position the first and second moveable legs are disposed at one of an oblique and perpendicular angle relative to an axis of the axially extending passageway.

9. The medical device of claim 1, wherein the sharpened surfaces comprise toothed surfaces configured to incise the tympanic membrane through a sawing action.

10. The medical device of claim 9, wherein the distal portions of the at least first and second movable legs include arcuate toothed surfaces.

11. The medical device of claim 10, further comprising third and fourth moveable legs operably coupled to the central portion.

12. The medical device of claim 9, wherein the toothed surfaces comprise serrated toothed surfaces.

13. The medical device of claim 1, further comprising third and fourth moveable legs.

14. The medical device of claim 1, wherein the sharpened surfaces comprise blade-shaped members having sharpened outer edges.

15. The medical device of claim 14, wherein the sharpened outer edges further comprise sharpened serrated outer edges.

16. The medical device of claim 14, wherein the sharpened outer edges are configured for back and forth movement across a surface of a tympanic membrane to facilitate a sawing of the tympanic membrane.

17. The medical device of claim 16, wherein the sharpened outer edges comprise arcuate sharpened outer edges.

18. The medical device of claim 1, wherein the radially extending flange is configured to reside in the external auditory canal, the central portion is configured to extend through the tympanic membrane, and the first and second moveable legs are configured to reside in the tympanic cavity in a maintenance position where the first and second legs are disposed at one of an oblique and perpendicular angle to the axis of the axially extending passageway.

19. A method for inserting a tympanostomy tube into and for continued residence in a tympanic membrane having an interiorly facing surface in the tympanic cavity and an exteriorly facing surface in the auditory canal, comprising:
providing a tympanostomy tube comprising a body including a first end portion, a second end portion, a central portion disposed between the first and second end portions, and an axially extending passageway having a first open end disposed adjacent the first end portion, and a second open end disposed adjacent the second end portion, and an axis extending between the first open end and second open end, the first end portion including a relatively enlarged diameter generally radially extending flange, the central portion including a reduced diameter portion sized for extending through and residing in tissue of the tympanic membrane, and the second end portion including at least first and second moveable legs having first ends coupled to the first end portion, and second ends, the second ends including sharpened toothed surfaces;

placing the toothed surfaces against the exteriorly facing surface of the tympanic membrane;

moving the tympanostomy tube in a back and forth direction to cause the toothed surfaces to engage the tympanic membrane and saw through the tympanic membrane; and positioning the tympanostomy tube in the tympanic membrane so that the tympanostomy tube resides in the tympanic membrane with the passageway operable to conduct air between the tympanic cavity and the auditory canal.

20. The method of inserting a tympanostomy tube of claim 19, wherein the step of positioning the tympanostomy tube in the tympanic membrane comprises positioning the tympanostomy tube in the tympanic membrane so that the at least first and second moveable legs reside in the tympanic cavity in a maintenance position, wherein the generally radially extending flange resides in the external auditory canal, and wherein the central portion extends through the tympanic membrane.

21. The method for inserting a tympanostomy tube of claim 20, wherein the sharpened toothed surfaces comprise serrated toothed surfaces.

\* \* \* \* \*